(12) United States Patent
Shusta et al.

(10) Patent No.: US 9,771,412 B2
(45) Date of Patent: Sep. 26, 2017

(54) ENGINEERED INTEIN FOR IMPROVED PRODUCTION OF PROTEIN-INTEIN FUSIONS

(71) Applicant: Wisconsin Alumni Research Foundation, Madison, WI (US)

(72) Inventors: Eric V. Shusta, Madison, WI (US); Carrie J. Marshall, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/926,665

(22) Filed: Oct. 29, 2015

(65) Prior Publication Data

US 2016/0122417 A1 May 5, 2016

Related U.S. Application Data

(60) Provisional application No. 62/073,498, filed on Oct. 31, 2014.

(51) Int. Cl.
| | |
|---|---|
| *C07K 14/47* | (2006.01) |
| *C07K 16/00* | (2006.01) |
| *C07K 14/35* | (2006.01) |
| *C12P 21/02* | (2006.01) |

(52) U.S. Cl.
CPC .............. *C07K 16/00* (2013.01); *C07K 14/35* (2013.01); *C12P 21/02* (2013.01); *C07K 2317/14* (2013.01); *C07K 2317/622* (2013.01); *C07K 2319/92* (2013.01)

(58) Field of Classification Search
CPC ............................ C07K 2319/92; C07K 14/47
See application file for complete search history.

(56) References Cited

U.S. PATENT DOCUMENTS

2016/0096872 A1* 4/2016 Shaw .................... C07K 14/575
530/350

OTHER PUBLICATIONS

Mohlmann et al. 2011; Site-specific modification of ED-B-targeting antibody using intein-fusion technology. BMC Biotechnology. 11:76, pp. 1-10.*
Natarajan, A., Xiong, C. Y., Albrecht, H., DeNardo, G. L., and DeNardo, S. J. (2005) Characterization of site-specific ScFv PEGylation for tumor-targeting pharmaceuticals, Bioconjugate chemistry 16, 113-121.
Sydor, J. R., Mariano, M., Sideris, S., and Nock, S. (2002) Establishment of Intein-Mediated Protein Ligation under Denaturing Conditions: C-Terminal Labeling of a Single-Chain Antibody for Biochip Screening, Bioconjugate Chemistry 13, 707-712.
Marshall, C. J., Agarwal, N., Kalia, J., Grosskopf, V. A., McGrath, N. A., Abbott, N. L., Raines, R. T., and Shusta, E. V. (2013) Facile chemical functionalization of proteins through intein-linked yeast display, Bioconjugate chemistry 24, 1634-1644.
Elias, D. R., Cheng, Z., and Tsourkas, A. (2010) An Intein-Mediated Site-Specific Click Conjugation Strategy for Improved Tumor Targeting of Nanoparticle Systems, Small 6, 2460-2468.
Kalia, J., and Raines, R. T. (2006) Reactivity of Intein Thioesters: Appending a Functional Group to a Protein, ChemBioChem 7, 1375-1383.
Guo, C., Li, Z., Shi, Y., Xu, M., Wise, J. G., Trommer, W. E., and Yuan, J. (2004) Intein-mediated fusion expression, high efficient refolding, and one-step purification of gelonin toxin, Protein Expression and Purification 37, 361-367.
Wood, R. J., Pascoe, D. D., Brown, Z. K., Medlicott, E. M., Kriek, M., Neylon, C., and Roach, P. L. (2004) Optimized Conjugation of a Fluorescent Label to Proteins via Intein-Mediated Activation and Ligation, Bioconjugate Chemistry 15, 366-372.
Cui, C., Zhao, W., Chen, J., Wang, J., and Li, Q. (2006) Elimination of in vivo cleavage between target protein and intein in the intein-mediated protein purification systems, Protein expression and purification 50, 74-81.
Wentz, A. E., and Shusta, E. V. (2008) Enhanced Secretion of Heterologous Proteins from Yeast by Overexpression of Ribosomal Subunit RPP0, Biotechnology Progress 24, 748-756.
Rakestraw, J. A., Sazinsky, S. L., Piatesi, A., Antipov, E., and Wittrup, K. D. (2009) Directed evolution of a secretory leader for the improved expression of heterologous proteins and full-length antibodies in *Saccharomyces cerevisiae*, Biotechnology and bioengineering 103, 1192-1201.
Adam, E., and Perler, F. B. (2002) Development of a positive genetic selection system for inhibition of protein splicing using mycobacterial inteins in *Escherichia coli* DNA gyrase subunit A, Journal of molecular microbiology and biotechnology 4, 479-488.
Shusta, E. V., Raines, R. T., Plückthun, A., and Wittrup, K. D. (1998) Increasing the secretory capacity of *Saccharomyces cerevisiae* for production of single-chain antibody fragments, Nature biotechnology 16, 773-777.
Hackel, B. J., Huang, D., Bubolz, J. C., Wang, X. X., and Shusta, E. V. (2006) Production of soluble and active transferrin receptor-targeting single-chain antibody using *Saccharomyces cerevisiae*, Pharmaceutical research 23, 790-797.
Wentz, A. E., and Shusta, E. V. (2007) A novel high-throughput screen reveals yeast genes that increase secretion of heterologous proteins, Applied and environmental microbiology 73, 1189-1198.
Miller, K. D., Weaver-Feldhaus, J., Gray, S. A., Siegel, R. W., and Feldhaus, M. J. (2005) Production, purification, and characterization of human scFv antibodies expressed in *Saccharomyces cerevisiae*, Pichia pastoris, and *Escherichia coli*, Protein expression and purification 42, 255-267.
Rostovtsev, V. V., Green, L. G., Fokin, V. V., and Sharpless, K. B. (2002) A stepwise huisgen cycloaddition process: copper (I)-catalyzed regioselective "ligation" of azides and terminal alkynes, Angewandte Chemie 114, 2708-2711.
Speers, A. E., Adam, G. C., and Cravatt, B. F. (2003) Activity-based protein profiling in vivo using a copper (I)-catalyzed azide-allcyne [3+2] cycloaddition, Journal of the American Chemical Society 125, 4686-4687.
Agard, N. J., Prescher, J. A., and Bertozzi, C. R. (2004) a Strain-Promoted [3+2] Azide-Alkyne Cycloaddition for Covalent Modification of Biomolecules in Living Systems, Journal of the American Chemical Society 126, 15046-15047.
Klabunde, T., Sharma, S., Telenti, A., Jacobs, W. R., and Sacchettini, J. C. (1998) Crystal structure of GyrA intein from *Mycobacterium xenopi* reveals structural basis of protein splicing, Nature Structural & Molecular Biology 5, 31-36.

* cited by examiner

*Primary Examiner* — Karen Cochrane Carlson
(74) *Attorney, Agent, or Firm* — Quarles & Brady, LLP

(57) ABSTRACT

The invention discloses engineered non-self-cleaving inteins derived from Mxe GyrA inteins and methods of using such inteins to chemically modify proteins.

51 Claims, 24 Drawing Sheets
(13 of 24 Drawing Sheet(s) Filed in Color)

Wild-type Mxe GyrA Intein

>DNA (SEQ ID NO:1)
TGCATCACGGGAGATGCACTAGTTGCCCTACCCGAGGGCGAGTCGGTACGCATCGC
CGACATCGTGCCGGGTGCGCGGCCCAACAGTGACAACGCCATCGACCTGAAAGTCC
TTGACCGGCATGGCAATCCCGTGCTCGCCGACCGGCTGTTCCACTCCGGCGAGCATC
CGGTGTACACGGTGCGTACGGTCGAAGGTCTGCGTGTGACGGGCACCGCGAACCAC
CCGTTGTTGTGTTTGGTCGACGTCGCCGGGGTGCCGACCCTGCTGTGGAAGCTGATC
GACGAAATCAAGCCGGGCGATTACGCGGTGATTCAACGCAGCGCATTCAGCGTCGA
CTGTGCAGGTTTTGCCCGCGGGAAACCCGAATTTGCGCCCACAACCTACACAGTCGG
CGTCCCTGGACTGGTGCGTTTCTTGGAAGCACACCACCGAGACCCGGACGCCCAAG
CTATCGCCGACGAGCTGACCGACGGGCGGTTCTACTACGCGAAAGTCGCCAGTGTC
ACCGACGCCGGCGTGCAGCCGGTGTATAGCCTTCGTGTCGACACGGCAGACCACGC
GTTTATCACGAACGGGTTCGTCAGCCACGCT

>Protein (SEQ ID NO:2)
CITGDALVALPEGESVRIADIVPGARPNSDNAIDLKVLDRHGNPVLADRLFHSGEHPVYT
VRTVEGLRVTGTANHPLLCLVDVAGVPTLLWKLIDEIKPGDYAVIQRSAFSVDCAGFAR
GKPEFAPTTYTVGVPGLVRFLEAHHRDPDAQAIADELTDGRFYYAKVASVTDAGVQPV
YSLRVDTADHAFITNGFVSHA

Figure 7

Clone 202-08
>DNA (SEQ ID NO:3)
TGCATCACGGGAGATGCACTAGTTGCCCTACCCGAGGGCGAGTCGGTACGCATCGC
CGACATCGTGCCGGGTGCGCGGCCCAACAGTGACAACGCCATCGACCTGAAAGTCC
TTGACCGGCATGGCAATCCCGTGCTCGCCGACCGGCTGCTCCACTCCGGCGAGCATC
CGGTGTACACGGTGCGTACGGTCGAAGGTCTGCGTGTGACGGGCACCGCGAACCAC
CCGTTGTTGTGTTTGGTCGACGTCGCCGGGGTGCCGACCCTGCTGTGGAAGCTGATC
GACGAGATCAAGCCGGGCGATTACGCGGTGGTTCAATGCAGCGCATCCAGCGTCGA
CTGTGCAGGTCTTGCCCGCGGGAAACCCGAACTTGCGCCCACAACCTACACAGTCG
GCGTCCCTGGACTGGTGCGTTTCTTGGAAGCACACCACCGAGACCCGGACGCCCAA
GCTATCGCCGACGAGCTGACCGACGGGCGGTTCTACTACGCGAAAGTCGCCGGTGT
CACCGACGCCGGCGTGCAGCCGGTGTATAGCCTTCGTGTCGACACGGCAGACCACG
CGTTTACCACGAACGGGTTCGTCAGCCACGCT >Protein (SEQ ID NO:4)
CITGDALVALPEGESVRIADIVPGARPNSDNAIDLKVLDRHGNPVLADRLLHSGEHPVYT
VRTVEGLRVTGTANHPLLCLVDVAGVPTLLWKLIDEIKPGDYAVVQCSASSVDCAGLA
RGKPELAPTTYTVGVPGLVRFLEAHHRDPDAQAIADELTDGRFYYAKVAGVTDAGVQP
VYSLRVDTADHAFTTNGFVSHA

Figure 8

Clone F2-02
>DNA (SEQ ID NO:5)
TGCATCACGGGAGATGCACTAGTTGCCCTACCCGAGGGCGAGTCGGTACGCATCGC
CGACATCGTGCCGGGTGCGCGGCCCAACAGTGACAACGCCATCGACCTGAAAGTCC
TTGATCGGCATGGCAATCCCGTGCTCGCCGACCGGCTGTTCCACTCCGGCGAGCATC
CGGTGTACACGGTGCGTACGGTCGAAGGTCTGCGTGTGACGGGCACCGCGAACCAC
CCGTTGTTGTGTTTGGTCGACGTCGCCGGGGTGCCGACCCTGCTGTGGAAGCTGATC
GACGAAATCAAGCCGGGCGATTACGCGGTGATTCAACGCAGCGCATTCAGCGCCGA
CCGTGCAGGTTTTACCCGCGGGAAACCCGAATTTGCGCCCACAACCTACACAGTCG
GCGTCCCTGGACTGGTGCGTTTCTTGGAAGCACACCGCCGAGACCCGGACGCCCAA
GCTATCGCCGACGAGCTGACCGACGGGCGGTTCTACTACGCGAAAGTCGCCGGTGT
CACCGACGCCGGCGTGCAGCCGGTGTATAGCCTTCGTGTCGACACGGCAGACCACG
CGTTTACCACGAACGGGTTCGTCAGCCACGCT >Protein (SEQ ID NO:6)
CITGDALVALPEGESVRIADIVPGARPNSDNAIDLKVLDRHGNPVLADRLFHSGEHPVYT
VRTVEGLRVTGTANHPLLCLVDVAGVPTLLWKLIDEIKPGDYAVIQRSAFSADRAGFTR
GKPEFAPTTYTVGVPGLVRFLEAHRRDPDAQAIADELTDGRFYYAKVAGVTDAGVQPV
YSLRVDTADHAFTTNGFVSHA

Figure 9

Clone F5-06
>DNA (SEQ ID NO:7)

TGCATCACGGGAGATGCACTAGTTGCCCTACCCGAGGGCGAGTCGGTACGCATCGC
CGGCATCGTGCCGGGTGCGCGGCCCAACAGTGACAACGCCATCGACCTGAAAGTCC
TTGACCGGCATGGCAATCCCGTGCTCGCCGACCGGCTGTTCCACTCCGGCGAGCATC
CGGTGTACACGGTGCGTACGGTCGAAGGTCTGCGTGTGACGGGCACCGCGAACCAC
CCGTTGTTGTGTTTGGTCGACGTCGCCGGGGTGCCGACCCTGCTGTGGAAGCTGATC
GACGAAATCAAGCCGGGCGATTACGCGGTGATTCAATGCAGCGCATCCAGCGTCGA
CGGTGCAGGTTTTACCCGCGGGAAACCCGAATTTGCGCCCACAACCTGCACAGTCG
GCGTCCCTGGACTGGTGCGTTTCTTGGAAGCACACCGCCGAGACCCGGACGCCCAA
GCTATCGCCGACGAGCTGACCGGCGGGCAGTTCTACTACGCGAAGGTCGCCAGTGT
CACCGACGCCGGCGTGCAGCCGGTGTATAGCCTTCGTGTCGACACGGCAGACCACG
CGTTTATCACGAACGGGTTCGTCAGCCACGCT

>Protein (SEQ ID NO:8)
CITGDALVALPEGESVRIAGIVPGARPNSDNAIDLKVLDRHGNPVLADRLFHSGEHPVYT
VRTVEGLRVTGTANHPLLCLVDVAGVPTLLWKLIDEIKPGDYAVIQCSASSVDGAGFTR
GKPEFAPTTCTVGVPGLVRFLEAHRRDPDAQAIADELTGGQFYYAKVASVTDAGVQPV
YSLRVDTADHAFITNGFVSHA

Figure 10

ENGINEERED INTEIN FOR IMPROVED PRODUCTION OF PROTEIN-INTEIN FUSIONS

CROSS-REFERENCE TO RELATED APPLICATIONS

This application claims the benefit of U.S. Provisional Patent Application No. 62/073,498, filed Oct. 31, 2014, which is incorporated herein by reference in its entirety for all purposes.

STATEMENT REGARDING FEDERALLY SPONSORED RESEARCH

This invention was made with government support under CA108467 awarded by the National Institutes of Health and 1403350 awarded by the National Science Foundation. The government has certain rights in the invention.

BACKGROUND OF THE INVENTION

The field of the invention is chemical modification of proteins and other biomolecules. Specifically, the present invention discloses engineered non-self-cleaving inteins of Mxe GyrA and methods of using such inteins to chemically modify proteins and other biomolecules.

Therapeutic and biochemical properties of proteins, such as antibodies, can be enhanced by custom chemical functionalization that enables modifications such as small molecule drug conjugation, PEGylation, and conjugation to nanoparticles. Expressed protein ligation (EPL) is one common approach to chemically modify proteins in a site-specific manner. In EPL, the target protein is expressed as a fusion partner to a non-self-cleaving intein such as Mxe GyrA.

Intein-mediated protein splicing is activated by the addition of a nucleophile, such as a thiol nucleophile, that releases the target protein from the intein while simultaneously producing a carboxy-terminal thioester intermediate on the target protein. Subsequently, this carboxy-terminal thioester can be reacted with an appropriately functionalized amino-terminal cysteine to covalently attach a desired moiety to the carboxy-terminus of the target protein.

Non-self-cleaving intein fusion proteins are most often expressed in the cytoplasm of *Escherichia coli*. One disadvantage of cytoplasmic expression is the formation of insoluble inclusion bodies that contain inactive protein-intein fusions, therefore requiring solubilization of the inclusion bodies and refolding of the protein. Glutathione redox buffers that are typically used to refold disulfide-containing proteins like antibodies can react with the thioester intermediate formed by the intein, thereby releasing it from the target protein and forming an unstable glutathione thioester on the carboxy-terminus of the target protein. This unstable glutathione thioester can subsequently be hydrolyzed leading to loss of the thioester functionality. Additionally, in vivo autocleavage of the intein has been observed during protein expression, resulting in up to 90% loss of the intein for some fusion proteins. These factors have combined to hamper protein-intein fusion protein production using bacteria.

Yeasts provide a possible alternative to bacterial expression systems, given their eukaryotic quality control machinery. In earlier work from Applicants' lab, scFvs were displayed as fusions to the Mxe GyrA intein on the surface of *Saccharomyces cerevisiae*. Contrasting with bacterial protein-intein fusion platforms, yeast-displayed scFv-intein protein fusions were properly folded and capable of engaging their antigenic targets. However, surface display levels of the scFvs were reduced by ~40% when fused to intein compared to the unfused antibody. In addition, surface display of heterologous proteins is not ideally suited for protein production at a preparative scale as the yield is too low (~70 μg of scFv/L).

Needed in the art are engineered non-self-cleaving inteins for significantly improving production of the resulting proteins with chemical functionalization. Specifically, needed in the art are engineered inteins and methods of using such inteins to improve yeast production of protein-intein fusions.

SUMMARY OF THE INVENTION

The present invention overcomes the aforementioned drawbacks by providing engineered inteins for improving yeast production of protein-intein fusions.

In one aspect, the present invention discloses an engineered intein for enhanced production of soluble fusion proteins in a yeast, wherein the engineered intein improves the fusion protein's display level at least by 1.4 fold and improve the fusion protein's secretion level at least by 4.4 fold as compared with the wild type intein.

In one embodiment, the engineered intein is a non-self-cleaving engineered Mxe GyrA intein. In one embodiment, the yeast is *Saccharomyces cerevisiae*.

In one embodiment, the engineered Mxe GyrA intein is clone 202-08 and expression products thereof (SEQ ID NOs:3 and 4) or an engineered Mxe GyrA intein comprising mutations at the same residues compared to wild-type Mxe GyrA intein as 202-08 but not necessarily the same substitutions.

In one embodiment, the engineered Mxe GyrA intein is clone F2-02 and expression products thereof (SEQ ID NOs:5 and 6) or an engineered Mxe GyrA intein comprising mutations at the same residues compared to wild-type Mxe GyrA intein as F2-02 but not necessarily the same substitutions.

In one embodiment, the engineered Mxe GyrA intein is clone F5-06 and expression products thereof (SEQ ID NOs:7 and 8) or an engineered Mxe GyrA intein comprising mutations at the same residues compared to wild-type Mxe GyrA intein as F5-06 but not necessarily the same substitutions.

In one embodiment, the engineered Mxe GyrA intein is selected from the group consisting of clones 202-08, F2-02, and F5-06.

In one embodiment, the engineered Mxe GyrA intein is configured to be used in expressed protein ligation (EPL).

In one embodiment, the present invention discloses an engineered Mxe GyrA intein for enhanced production of soluble fusion proteins in a host cell, wherein the engineered Mxe GyrA intein is selected from the group consisting of clones 202-08, F2-02, and F5-06 or an engineered Mxe GyrA intein comprising mutations at the same residues compared to wild-type Mxe GyrA intein as 202-08, F2-02, and F5-06 but not necessarily the same substitutions.

In one embodiment, the present invention discloses an engineered Mxe GyrA intein for enhanced production of soluble fusion proteins in a host cell, wherein the engineered Mxe GyrA intein is selected from the group consisting of inteins comprising at least 3 of the mutations found in clones 202-08, F2-02, or F5-06.

In one embodiment, the intein comprises at least 4 of the mutations.

In another aspect, the present invention discloses a kit for enhancing production of soluble fusion proteins in yeast, wherein the kit comprises at least one engineered intein, wherein the engineered intein improves the fusion protein's display level at least by 1.4 fold and improves the fusion protein's secretion level at least by 4.4 fold as compared with the wild type intein.

In one embodiment, the engineered intein is a non-self-cleaving engineered Mxe GyrA intein.

In one embodiment, the engineered Mxe GyrA intein is selected from the group consisting of clone 202-08 (SEQ ID NOs:3 and 4), clone F2-02 (SEQ ID NOs:5 and 6), and clone F5-06 (SEQ ID NOs:7 and 8) and expression products thereof.

In one embodiment, the kit additionally comprising a nucleophile.

In one embodiment, the present invention discloses a kit for enhancing production of soluble fusion proteins in a host cell, wherein the kit comprises at least one engineered Mxe GyrA intein selected from the group consisting of clone 202-08 (SEQ ID NOs:3 and 4), clone F2-02 (SEQ ID NOs:5 and 6), and clone F5-06 (SEQ ID NOs:7 and 8) and expression products thereof, an engineered Mxe GyrA intein comprising mutations at the same residues compared to wild-type Mxe GyrA intein as 202-08, F2-02, and F5-06 but not necessarily the same substitutions and an engineered Mxe GyrA intein consisting of inteins comprising at least 3 of the mutations found in clones 202-08, F2-02, or F5-06.

In another aspect, the present invention discloses a method for chemically functionalizing a protein of interest in a yeast, the method comprising the steps of (a) obtaining an engineered intein, wherein the intein is a non-self-cleaving engineered Mxe GyrA intein; (b) expressing the protein as a fusion partner with the engineered intein in the yeast to form an intein-protein complex; and (c) adding a first compound having a nucleophile and a functional group to the complex, wherein the nucleophile reacts with the intein-protein complex to release the protein of interest from the intein-protein complex, wherein the protein is chemically linked to the functional group.

In one embodiment, the protein is an antibody.

In one embodiment, the engineered intein is selected from the group consisting of engineered Mxe GyrA intein clone 202-08 (SEQ ID NOs:3 and 4), clone F2-02 (SEQ ID NOs:5 and 6), and clone F5-06 (SEQ ID NOs:7 and 8) and expression products thereof and an engineered Mxe GyrA intein comprising mutations at the same residues compared to wild-type Mxe GyrA intein as 202-08, F2-02, and F5-06 but not necessarily the same substitutions, and an engineered Mxe GyrA intein consisting of inteins comprising at least 3 of the mutations found in clones 202-08, F2-02, or F5-06.

In one embodiment, the protein is chemically functionalized via expressed protein ligation (EPL).

In one embodiment, the yeast is *Saccharomyces cerevisiae*.

In one embodiment, the engineered Mxe GyrA intein improves a fusion protein display level at least by 1.4 fold and improves the fusion protein secretion level at least by 4.4 fold as compared with the wild type intein.

In one embodiment, the intein-protein complex in step (b) is further purified.

In one embodiment, the first compound is 2-mercapthoe-thanesulfonic acid (MESNA).

In another aspect, the present invention discloses a method for chemically functionalizing a protein of interest in a host cell. The method comprises the steps of (a) obtaining an engineered Mxe GyrA intein selected from the group consisting of clone 202-08 (SEQ ID NOs:3 and 4), clone F2-02 (SEQ ID NOs:5 and 6), and clone F5-06 (SEQ ID NOs:7 and 8) and expression products thereof, an engineered Mxe GyrA intein comprising mutations at the same residues compared to wild-type Mxe GyrA intein as clones 202-08, F2-02, and F5-06 but not necessarily the same substitutions, and an engineered Mxe GyrA intein consisting of inteins comprising at least 3 of the mutations found in clones 202-08, F2-02, or F5-06; (b) expressing the protein of interest as a fusion partner with the engineered Mxe GyrA intein to form an intein-protein complex; and (c) adding a first compound having a nucleophile and a functional group to the complex, wherein the nucleophile of the compound reacts with the complex to release the protein from the complex, wherein the protein is chemically linked to the functional group.

In one embodiment, the host is selected from the group consisting of bacterial, yeast, mammalian and fungal cells.

In one embodiment, the protein is chemically functionalized via expressed protein ligation (EPL).

In one embodiment, the intein-protein complex in step (b) is further purified.

In one embodiment, the first compound is 2-mercapthoe-thanesulfonic acid (MESNA).

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1a: In display construct pCT4Re, Aga2p is expressed at the carboxy-terminus to anchor the fusion protein to the yeast surface, while a FLAG epitope tag is expressed on the amino-terminus of the scFv or GFP to indicate full-length construct expression on the yeast surface. In the intein-containing display constructs, the non-self-cleaving Mxe GyrA intein is inserted between the carboxy-terminus of the scFv or GFP and the Aga2p surface anchor. FIG. 1b: Secretion construct pRS316-FLAG is similar to the surface display construct, with a synthetic pre-pro leader sequence directing secretion and a six histidine epitope for purification.

FIG. 2a: For directed evolution round 1, the Mxe GyrA intein library was created by random mutagenesis and recombined into the pCT4Re-4420 construct. The library was screened in four rounds of enrichment for improved FLAG tag expression via FACS. A fifth round of enrichment selected for both improved FLAG tag expression and commensurate increases in fluorescein binding. Individual clones were isolated and screened for intein activity by the addition of MESNA, which releases the scFv from the display construct when an active intein is present. For directed evolution round 2, the round 1 clones were shuffled and mutagenized prior to screening for increased display levels. FIG. 2b: Flow cytometry dot plots depicting expression and binding activity of scFv-intein clones and pools on the yeast surface. Geometric mean fluorescence intensity (MFI) of the FLAG signal for the entire displaying population is shown to allow comparison. In addition, a sample sort gate is shown to illustrate the enrichment. Panel i, wild-type intein fusion; panel ii, round 1 final selected pool; panel iii, round 2 final selected pool, panel iv, unfused 4-4-20 scFv; panel v, round 1 202-08 intein mutant. FIG. 2c: The MFI of the displaying population was quantified and normalized to the wildtype 4-4-20-intein construct to compare the relative expression levels (FLAG) and activity (fluorescein binding) of the unfused 4-4-20 construct, wild-type intein construct, and the 202-08 intein mutant. Activity per molecule is expressed as the ratio of fluorescein binding to FLAG expression level. Plotted are the means±S.D. from three independent yeast transformants. Statistically significant improvements over the wild-type intein construct were determined by an unpaired Student's t-test (*, $p<0.05$; **, $p<0.01$; NS, not significant $p>0.05$). Display data for other individual intein mutants are compiled in Table 1. FIG. 2d: Quantitative anti-FLAG Western blotting was performed to determine the relative amount of 4-4-20 released from the yeast surface in the MESNA reaction. Plotted are means±S.D. for three independent reactions originating from three independent yeast surface display transformants. Next to the bar graph are the triplicate Western blot data at the cleaved scFv size of ~30 kDa. A small amount of the uncleaved, scFv-intein product appears at a size of ~90 kDa due to its fusion to glycosylated Aga2p. The double asterisk represents a statistically significant increase in 4-4-20 release for clone 202-08 ($p<0.01$) as determined by an unpaired Student's t-test. FIG. 2e: The crystal structure of the Mxe GyrA intein (pdb ID: 1AM263) is shown with the mutations found in the 202-08 intein highlighted. A flexible loop missing from the crystal structure is denoted by a dotted line and the structure on the right was rotated 90°.

FIG. 3a: Surface display levels of unfused, wild-type intein fused or 202-08 intein fused scFvs and GFP were analyzed by flow cytometry. The MFI of the FLAG-positive yeast populations was quantified, and all were normalized to the 4-4-20 construct containing the wild-type intein. Reported are the means±S.D. of three independent yeast transformants. Statistical analysis was performed by an unpaired Student's t-test (*, $p<0.05$; **, $p<0.01$; NS, not significant $p>0.05$). FIG. 3b: ScFv and GFP per molecule activity was evaluated by detecting binding to the scFv antigens at saturating ligand concentrations or by measuring GFP fluorescence. Activity per molecule was determined by calculating the ratio of the geometric means for activity (binding or fluorescence) to FLAG expression levels and normalizing to the unfused construct lacking intein. Plotted are the means±S.D. from three independent yeast transformants, with statistical significance determined by an unpaired Student's t-test (*, $p<0.05$; **, $p<0.01$; NS, not significant $p>0.05$). FIG. 3c: For intein mediated protein release, MESNA reacts to release the scFv or GFP from the display construct and append a carboxy-terminal thioester. For EPL functionalization, the carboxy-terminal thioester reacts with a biotinylated peptide containing an amino-terminal cysteine to covalently link the scFv or GFP to the biotin by an amide bond.

FIG. 4a: Yeast supernatants containing scFv or GFP fused to the wild-type intein or 202-08 intein were subjected to anti-FLAG quantitative Western blotting and compared to the unfused target protein. Values are normalized to the level of the 4-4-20-202-08 fusion to determine relative amounts. The absolute secretion titer of the 4-4-20-202-08 fusion protein is 3.1 mg/L as determined in panel b). Reported are the means±S.D. from three independent yeast transformants. Statistical significance was determined by an unpaired Student's t-test (*, $p<0.05$; , $p<0.01$; NS, not significant $p>0.05$). Western blot of supernatant samples used for the quantization of relative 4-4-20 protein secretion is shown below the bar graph. FIG. 4b: An equilibrium binding curve was generated by fluorescein quenching to compare the Kd of unfused 4-4-20 and 4-4-20 fused to 202-08. A sample curve for each of the proteins is shown, and the mean±S.D for the fitted parameters of Kd value and 4-4-20 concentration were obtained by fitting quench curves generated from supernatants resulting from three independent yeast transformants. From the molar concentrations of 4-4-20, the average mass concentration of the 4-4-20 component was calculated to be 1.6 mg/L of yeast culture for both the unfused and the intein-fused 4-4-20 (corresponding to 3.1 mg/L for the full 4-4-20-202-08 fusion protein) The Kd and 4-4-20 concentrations were statistically indistinguishable, as determined by an unpaired Student's t-test ($p>0.05$). FIG. 4c: GFP activity was determined by calculating the ratio of fluorescence to FLAG expression levels and normalizing to the unfused construct lacking intein. The mean±S.D results from three independent yeast transformants. The fluorescence per molecule of unfused GFP and 202-08 fused GFP was statistically indistinguishable, as determined by an unpaired Student's t-test (, $p>0.05$). FIG. 4d: The catalytic activity of 202-08 was examined by reacting secreted and purified proteins with MESNA and evaluating cleaved yield after standard 20 h reaction. Anti-FLAG Western blotting demonstrates between 70% (2224) and 99% (MR1) release of the target protein from the 202-08 intein in the presence of MESNA.

FIG. 5a: Secreted and purified scFv and GFP proteins fused to the 202-08 intein were released with MESNA to form scFv- and GFPthioesters. The carboxy-terminal thioesters were subsequently reacted with a cysteine azide via EPL to install an azido group onto the protein. To immobilize the proteins on surfaces, the scFv- and GFP-azide proteins were reacted with DBCO-functionalized agarose beads in a strain promoted click chemistry reaction. FIG. 5b: Fluorescent microscope images of GFP fluorescence associated with beads reacted with GFP-azide or non-azido GFP (GFP-thioester). Relative protein immobilization was quantified by measuring total bead fluorescence and normalizing to the azide-GFP loaded beads. The mean±S.D. of three independent immobilization reactions is plotted. Statistical significance was determined by an unpaired Student's t-test (, $p<0.01$). FIG. 5c: Binding of fluorescein to beads reacted with azide functionalized 4-4-20 was analyzed and compared to beads reacted with azide-linked scFv2. FITC-dextran binding was quantified by measuring the fluorescence intensity of the beads, and the fluorescence was normalized to the 4-4-20-linked sample. Three independent immobilization reactions were carried out to obtain the mean±S.D. values. An unpaired Student's t-test was performed to determine statistical significance (, p<0.01).

FIG. 5d: Immobilized EGFR scFv activity was assessed by EGFR capture from cell lysates. Fluorescent microscopy images were employed to demonstrate EGFR capture and EGFR isoform specificity. A431 cells express wild-type EGFR while U87 cells are transfected to express the EGFR vIII isoform. ScFv activity was quantified by measuring the resulting fluorescence intensity of the beads, and the fluorescence value was normalized to the signal originating from the U87-EGFRvIII lysate binding to the respective scFv. The fluorescence value for the negative control, 4-4-20, was normalized to the signal originating from the U87-EGFRvIII binding to MR1. The mean±S.D. of three independent immobilization reactions is plotted. Statistical significance was determined by an unpaired Student's t-test (**, p<0.01).

FIG. 7 shows DNA and protein sequences listings of Wild-type Mxe GyrA Intein.

FIG. 8 shows DNA and protein sequences listings of engineered Mxe Gyra Intein Clone 202-08. Residue changes from the wild-type intein are highlighted in yellow and are bolded.

FIG. 9 shows DNA and protein sequences listings of engineered Mxe Gyra Intein Clone F2-02. Residue changes from the wild-type intein are highlighted in yellow and are bolded.

FIG. 10 shows DNA and protein sequences listings of engineered Mxe Gyra Intein Clone F5-06. Residue changes from the wild-type intein are highlighted in yellow and are bolded.

DETAILED DESCRIPTION OF THE INVENTION

Figure 1A:
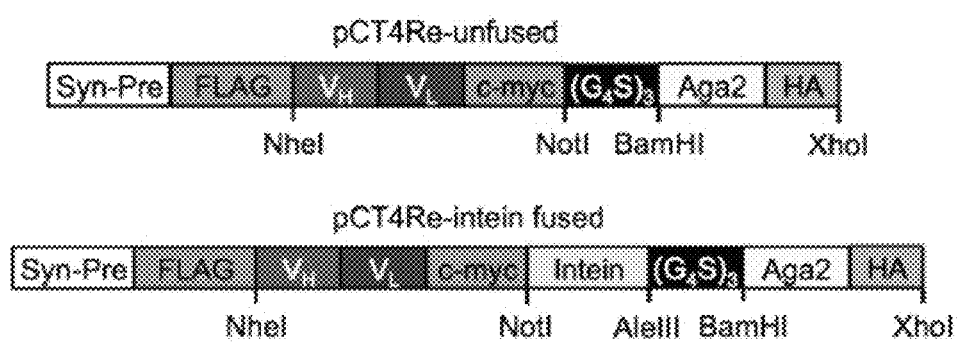
FIGS. 1a and 1b are diagrams showing surface display and secretion constructs.

The term "intein," as used herein, refers to a segment of a protein that is able to excise itself and join the remaining portions (the exteins) with a peptide bond in a process termed protein splicing. Inteins have also been called "protein introns". Intein-mediated protein splicing occurs after the intein-containing mRNA has been translated into a protein. This precursor protein contains three segments—an N-extein followed by the intein followed by a C-extein. After splicing has taken place, the resulting protein contains the N-extein linked to the C-extein; this splicing product is also termed an extein. In one embodiment, the inteins of the present invention are non-self-cleaving inteins. The non-self-cleaving inteins do not cleave from the fusion protein unless suitable external conditions (e.g., presence of a nucleophile) occur.

The term "engineered intein," as used herein, refers to an intern including at least one, two, three, four, five, six, seven, eight, nine, ten or more amino acid mutations compared to the wild type intein.

The term "Mxe GyrA intein," as used herein, refers to an intein from *Mycobacterium xenopi* of 198 amino acids in length. FIG. 7 shows DNA and protein sequences listings of wild-type Mxe GyrA Intein (SEQ ID NOs: 1-2).

The term "engineered Mxe GyrA intein," as used herein, refers to a Mxe GyrA intein including at least one, two, three, four, five, six, seven, eight, nine, ten or more amino acid mutations compared to the wildtype Mxe GyrA intein. Preferably, the engineered Mxe GyrA intein in the present invention includes at least five, six, seven, or eight amino acid mutations compared to the wildtype Mxe GyrA intein.

The term "protein splicing," as used herein, refers to an intramolecular reaction of a particular protein in which an internal protein segment (called an intein) is removed from a precursor protein with a ligation of C-terminal and N-terminal external proteins (called exteins) on both sides. The splicing junction of the precursor protein is typically a cysteine or a serine, which are amino acids containing a nucleophilic side chain. The protein splicing reactions which are known now do not require exogenous cofactors or energy sources such as adenosine triphosphate (ATP) or guanosine triphosphate (GTP). Normally, splicing is associated only with pre-mRNA splicing.

The term "nucleophile," as used herein, refers to any chemical species that donates an electron pair to an electrophile to form a chemical bond in relation to a reaction. All molecules or ions with a free pair of electrons or at least one pi bond can act as nucleophiles. Because nucleophiles donate electrons, they are by definition Lewis bases. In one embodiment of the present invention, a nucleophile may be either a sulfur nucleophile or a nitrogen nucleophile.

The term "sulfur nucleophile," as used herein, refers to a nucleophile comprising at least one sulfur atom. The example of sulfur nucleophile may include hydrogen sulfide and its salts, thiols (RSH), thiolate anions (RS$^-$), anions of thiolcarboxylic acids (RC(O)—S$^-$), and anions of dithiocarbonates (RO—C(S)—S$^-$) and dithiocarbamates (R$_2$N—C(S)—S$^-$). In one preferred embodiment of the present invention, the sulfur nucleophile is MESNA or DTT.

The term "nitrogen nucleophile," as used herein, refers to a nucleophile comprising at least one nitrogen atom. Nitrogen nucleophiles include ammonia, azide, amines, hydrazines, and nitrites. In one preferred embodiment of the present invention, the nitrogen nucleophile is hydrazine.

The term "leaving group," as used herein, refers to groups readily displaceable by a nucleophile, such as an amine, alcohol, phosphorous or thiol nucleophile or their respective anions. Such leaving groups are well known and include carboxylates, N-hydroxysuccinimide, N-hydroxybenzotriazole, halogen (halides), triflates, tosylates, mesylates, alkoxy, thioalkoxy, phosphinates, phosphonates, sulfonates and the like. In one preferred embodiment, the leaving groups of the present invention are sulfonates. Other potential nucleophiles include organometallic reagents known to those skilled in the art. In addition, the term "leaving group" or "LG" is meant to encompass leaving group precursors (i.e., moieties that can be easily converted to a leaving group upon simple synthetic procedures such as alkylation, oxidation or protonation). Such leaving group precursors and methods for converting them to leaving groups are well known to those of ordinary skill in the art. Leaving group precursors include, for instance, secondary and tertiary amines.

The term "biomolecule," as used herein, refers generally to molecules of biological origin, such as, for example, nucleic acids, peptides, combinations and complexes thereof, and/or other appropriate biologically generated molecules. Biomolecule may also refer to the both an expression vector encoding a functional product and the functional product itself. In one embodiment, the biomolecule in the present invention is a protein. In another embodiment, the biomolecule in the present invention is an antibody.

The terms "polypeptide," "peptide," and "protein," as used herein, refer to a polymer comprising amino acid residues predominantly bound together by covalent amide bonds. By the term "protein," we mean to encompass all the above definitions. The terms apply to amino acid polymers in which one or more amino acid residue may be an artificial chemical mimetic of a naturally occurring amino acid, as well as to naturally occurring amino acid polymers and non-naturally occurring amino acid polymers. As used herein, the terms may encompass amino acid chains of any length, including full length proteins, wherein the amino acids are linked by covalent peptide bonds. The protein or peptide may be isolated from a native organism, produced by recombinant techniques, or produced by synthetic production techniques known to one skilled in the art.

The term "recombinant protein," as used herein, refers to a polypeptide of the present disclosure which is produced by recombinant DNA techniques, wherein generally, DNA encoding a polypeptide is inserted into a suitable expression vector which is in turn used to transform a heterologous host cell (e.g., a microorganism or yeast cell) to produce the heterologous protein.

The term "recombinant nucleic acid" or "recombinant DNA," as used herein, refers to a nucleic acid or DNA of the present disclosure which is produced by recombinant DNA techniques, wherein generally, DNA encoding a polypeptide is inserted into a suitable expression vector which is in turn used to transform a host cell to produce the heterologous protein.

The term "fusion protein," as used herein, refers to a hybrid polypeptide which comprises protein domains from at least two different proteins. Fusion proteins or chimeric proteins (literally, made of parts from different sources) are proteins created through the joining of two or more genes that originally coded for separate proteins. Translation of this fusion gene results in a single or multiple polypeptides with functional properties derived from each of the original proteins. Recombinant fusion proteins are created artificially by recombinant DNA technology for use in biological research or therapeutics. Chimeric or chimera usually designate hybrid proteins made of polypeptides having different functions or physico-chemical patterns. Chimeric mutant proteins occur naturally when a complex mutation, such as a chromosomal translocation, tandem duplication, or retrotransposition creates a novel coding sequence containing parts of the coding sequences from two different genes. Naturally occurring fusion proteins are commonly found in cancer cells, where they may function as oncoproteins. In one embodiment of the present invention, fusion proteins comprise at least one engineered intein.

The term "antibody," as used herein, refers to a class of proteins that are generally known as immunoglobulins. The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

The term "lyophilization," as used herein, refers to freezing of a material at low temperature followed by dehydration by sublimation, usually under a high vacuum. Lyophilization is also known as freeze drying. Many techniques of freezing are known in the art of lyophilization such as tray-freezing, shelf-freezing, spray-freezing, shell-freezing and liquid nitrogen immersion. Each technique will result in a different rate of freezing. Shell-freezing may be automated or manual. For example, flasks can be automatically rotated by motor driven rollers in a refrigerated bath containing alcohol, acetone, liquid nitrogen, or any other appropriate fluid. A thin coating of product is evenly frozen around the inside "shell" of a flask, permitting a greater volume of material to be safely processed during each freeze drying run. Tray-freezing may be performed by, for example, placing the samples in lyophilizer, equilibrating 1 hr at a shelf temperature of 0° C., then cooling the shelves at 0.5° C./min to −40° C. Spray-freezing, for example, may be performed by spray-freezing into liquid, by dropping ~20 µl droplets into liquid $N_2$, spray-freezing into vapor over liquid, or by other techniques known in the art.

The term "yeast," as used herein, refers to the classification Fungi, eukaryotic microorganisms having cell wall, cell membrane and intracellular components. Yeast does not form a specific taxonomic grouping or phylogenetic studies. Any suitable yeast as appreciated by one skilled in the art may be used for the present invention. U.S. Pat. Ser. No. 8,034,607 describes some exemplary yeasts, which are suitable for the present invention. In one preferred embodiment, the yeast in the present invention is *Saccharomyces cerevisiae*.

The term "improve," as used herein, refers to the target property (e.g., display level) which has been increased by at least, 1.4, 1.5, 1.6, 1.7, 1.8, 1.9 or 2.0 fold. In one embodiment, the target property (e.g., secretion level) is increased by at least 1.5, 1.7, 2, 3, 4, 5, 6, 7, 8, 9, 10, 11, 12, 13, 14, 15, 16, 17, 18, 19, or 20 fold.

The term "functional group," as used herein, refers to any chemical unit that can be attached, such as by any stable physical or chemical association, to a biomolecule in the present invention, thereby rendering chemical functionalization of the biomolecule. A functional group may be also referred to herein as a reactive functional group.

The term "expressed protein ligation" or "EPL," as used herein, refers to a protein semi-synthesis method that permits the in vitro ligation of a chemically synthesized C-terminal segment of a protein to a recombinant N-terminal segment fused through its C terminus to an intein protein splicing element. In principle, the practical convenience of this method, combined with the expanded opportunities in protein engineering that it provides, makes it well suited for probing the molecular basis of complex processes such as transcription. Tom W. Muir has recently systematically described EPL in Semisynthesis Of Proteins By Expressed Protein Ligation, Annual Review of Biochemistry, 2003, Vol. 72: 249-289.

The term "click chemistry," as used herein, refers to chemical synthesis tailored to generate substances quickly and reliably by joining small units together. "Click chemistry" is not a single specific reaction, but describes a way of generating products that follows examples in nature, which also generates substances by joining small modular units. In one embodiment of the present invention, click chemistry may include methods for producing proteins through chemical synthesis.

The Engineered Inteins:

In one aspect, the present invention discloses engineered inteins for enhanced production of fusion proteins in a yeast, wherein the engineered intein improves both the fusion proteins display level and the fusion proteins secretion level significantly as compared with the wild type intein. In another embodiment, the present invention provides engineered inteins for use in microorganism or eukaryotic host cells, including yeast, bacterial, mammalian and fungal cells.

In one specific embodiment, the engineered intein improves fusion protein display level in a yeast host at least by 1.4 fold and improves fusion protein secretion level by at least 4.4 fold as compared with the wild type intein.

In different embodiments, the engineered inteins may be self-cleaving inteins or non-self-cleaving inteins.

In one embodiment, the engineered inteins of the present invention may be self-cleaving inteins. For example, Applicants envision that the 202-08 clone (described below) plus reversion of the 198Asn mutation would produce a self-cleaving Mxe GyrA intein. Specifically, the self-cleaving Mxe GyrA intein would require mutating residue 198 in the 202-08 clone from Ala to Asn as the self cleaving version has 198N and the non-self cleaving is 198A.

In one embodiment, described below and in the Examples, the engineered inteins are non-self-cleaving inteins.

In one embodiment, the engineered intein is a non-self-cleaving engineered Mxe GyrA intein. In one embodiment, the engineered Mxe GyrA intein has at least 1, 2, 3, 4, 5, 6, 7, 8, 9, 10, 11, 12, 13, 14, 15, 16, 17, 18, 19 or 20 amino acid mutations relative to the wild type. In one preferred embodiment, the engineered Mxe GyrA intein has at least 3, 4, 5, 6, 7, 8, 9, 10, 11, 12, 13, or 14 amino acid mutations relative to the wild type. More preferably, the engineered Mxe GyrA intein has at least 4, 5, 6, 7, or 8, amino acid mutations relative to the wild type.

In one specific embodiment, the present engineered Mxe GyrA intein is clone 202-08 and expression products thereof (SEQ ID NOs:3 and 4). FIG. 8 shows DNA and protein sequences listings of engineered Mxe Gyra Intein Clone 202-08. As shown in FIG. 8, clone 202-08 includes eight amino acid mutations (also see Tables 1-2 and FIG. 2e). The eight amino acid mutations include F51L, I105V, R107C, F110S, F117L, F124L, S168G and I190T. In another embodiment of the present invention, the engineered Mxe GryA intein will have at least 2, 3, 4, 5, 6, or 7 of these mutations. In another embodiment, the engineered Mxe GyrA intein will have mutated residues at the same location as described above, but the substituting residue will be different in at least one of the mutations.

Figure 3A:
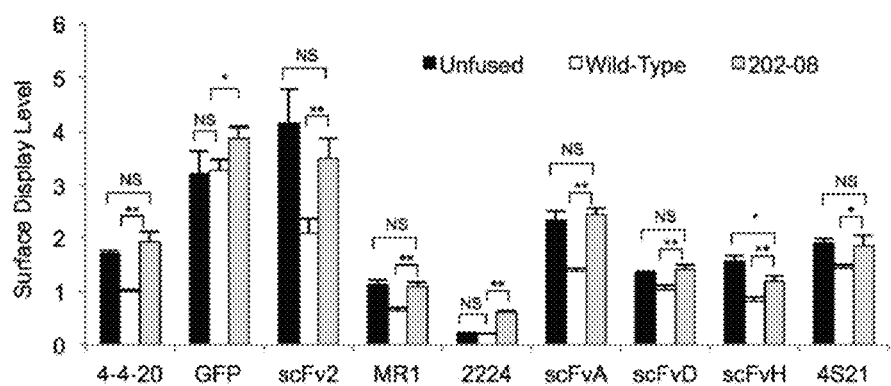
FIGS. 3a, 3b, and 3c are graphs and diagrams showing analysis of surface displayed scFv- and GFP-202-08 fusions.

FIG. 3a shows that the surface display level of the fusion protein having clone 202-08 is at least comparable to that of the corresponding wild type. Tables 1 and 2 demonstrate that clone 202-08 improves the fusion protein's display level at least by 1.8 fold and improves the fusion protein's secretion level at least by 10.4 fold as compared with the wild type intein.

In another specific embodiment, the present engineered Mxe GyrA intein is clone F2-02 and expression products thereof (SEQ ID NOs:5 and 6). FIG. 9 shows DNA and protein sequences listings of engineered Mxe GyrA Intein Clone F2-02. As shown in FIG. 9, clone F2-02 includes five amino acid mutations (also see Table 2). The five amino acid mutations include V112A, C114R, A118T, H144R, and S168G. In another embodiment of the present invention, the engineered Mxe GryA intein will have at least 2, 3 or 4 of these mutations. In another embodiment, the engineered Mxe GyrA intein will have mutated residues at the same location as described above, but the substituting residue will be different in at least one of the mutations.

Table 2 demonstrates that the clone F2-02 improves the fusion protein's display level at least by 1.4 fold and improves the fusion protein's secretion level at least by 6.5 fold as compared with the wild type intein.

In yet another specific embodiment, the present engineered Mxe GyrA intein is clone F5-06 and expression products thereof (SEQ ID NOs:7 and 8).

FIG. 10 shows DNA and protein sequences listings of engineered Mxe Gyra Intein Clone F5-06. As shown in FIG. 10, clone F5-06 includes eight amino acid mutations (also see Table 2). The eight amino acid mutations include R107C, F110S, C114G, A118T, Y129C, H144R, D158G, and R160Q. In another embodiment of the present invention, the engineered Mxe GryA intein will have at least 2, 3, 4, 5, 6, or 7 of these mutations. In another embodiment, the engineered Mxe GyrA intein will have mutated residues at the same location as described above, but the substituting residue will be different in at least one of the mutations.

Table 2 demonstrates that the clone F5-06 improves the fusion protein's display level at least by 1.4 fold and improves the fusion protein's secretion level at least by 4.4 fold as compared with the wild type intein.

In one embodiment, the present engineered Mxe GyrA intein is selected from the group consisting of clones 202-03, 202-08, 202-12, 202-13, 505-05, 505-11, F1-01, F1-12, F1-16, F2-02, F2-05, F2-08, F2-18, F5-03, F5-06 and expression products thereof.

Tables 1 and 2 demonstrate that clones 202-03, 202-08, 202-12, 202-13, 505-05, 505-11, F1-01, F1-12, F1-16, F2-02, F2-18, F2-05, F2-08, F5-03, and F5-06 at least improve the fusion proteins display level or the fusion proteins secretion level as compared with the wild type intein.

Applicants show below how Mxe GyrA inteins may be produced through a method of directed evolution. However, one using the present invention may wish to create the intein directly. Applicants envision that non-self-cleaving engineered Mxe GyrA inteins as discussed above in the present invention may be produced from any suitable method such as subcloning the as-disclosed gene sequence into any fusion construct of interest to produce the protein of interest.

In one embodiment, non-self-cleaving engineered Mxe GyrA inteins may be produced through a method of directed evolution. Example 1 demonstrates the present engineered Mxe GyrA inteins can be produced through directed evolution. For example, Applicants found that the surface display levels of scFv-intein fusions are generally 25-50% reduced compared to the unfused scFv, thus providing a convenient screening pressure of improved yeast display.

Figure 2A:
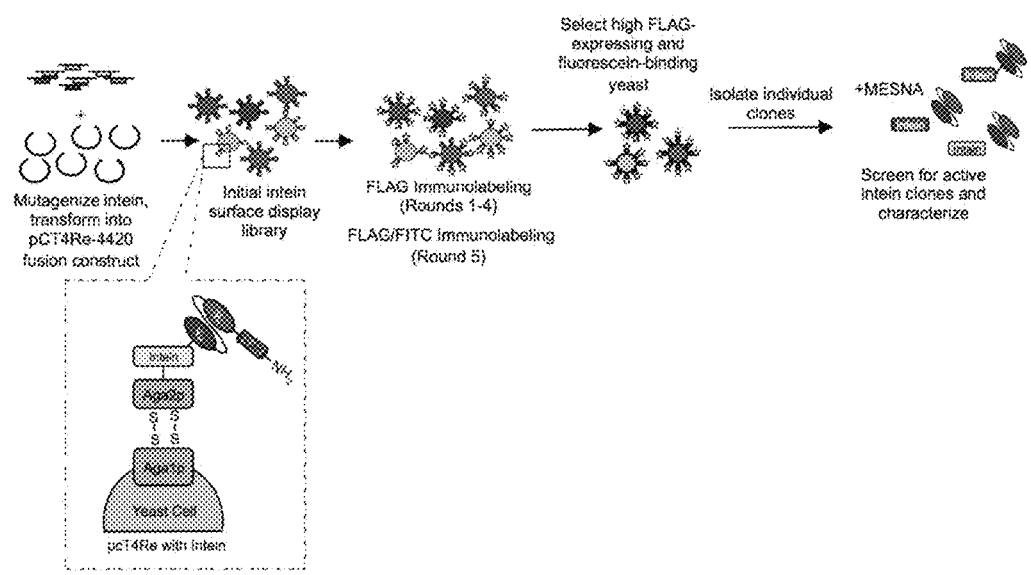
FIGS. 2a, 2b, 2c, 2d, and 2e are diagrams and graphs showing directed evolution of the Mxe GyrA intein.

FIG. 2a shows directed evolution for producing the engineered Mxe GyrA inteins. For directed evolution round 1, the engineered Mxe GyrA intein library was created by random mutagenesis and recombined into the pCT4Re-4420 construct.

Applicants envision that other constructs may also be used for the present invention. For example, the strategy in the present invention may be applied to any fusion protein partner of interest by replacing 4-4-20 (described below) with a protein of interest. Moreover, the intein-protein fusion may be displayed using any display platform. Suitable display platforms may include those that allows the intein-protein fusion to be connected to the N-terminus of the display protein. One example is a traditional yeast surface display via the Aga2p protein. Other examples of display platform include using Aga1p or Flo1p as a fusion partner.

In one specific embodiment, the engineered Mxe GyrA intein library may be screened in four rounds of enrichment for improved FLAG tag expression via FACS. Applicants envision that any other affinity tag may also be used for screening the engineered Mxe GyrA intein library in the present invention. A suitable tag may include the V5 tag, the HA tag (from hemagglutinin influenza virus), the myc tag, and the like, as is known in the art. Suitable affinity tags may also include domains for which binding substrates are known, e.g., HIS, GST and MBP tags, as is known in the art, and domains from other proteins for which specific binding partners, e.g., antibodies, particularly monoclonal antibodies, are available. Suitable affinity tags also include any protein-protein interaction domain, such as an IgG Fc region, which may be specifically bound and detected using a suitable binding partner, e.g. the IgG Fc receptor.

In one embodiment, a fifth round of enrichment selected for both improved FLAG tag expression and commensurate increases in fluorescein binding. Individual engineered Mxe GyrA intein clones may be isolated and screened for intein activity by the addition of a nucleophile such as MESNA, which releases the scFv from the display construct when an active intein is present.

In one embodiment, for directed evolution round 2, the round 1 engineered Mxe GyrA intein clones may be shuffled and mutagenized prior to screening for increased display levels.

In one embodiment, the present engineered inteins and the fusion proteins may be expressed in a yeast. In one specific embodiment, the yeast is *Saccharomyces cerevisiae*. Applicants envision that any other yeast may also be used as a suitable expression medium for the present invention.

In one embodiment, the present engineered inteins may be used for site-specific chemical modification of a biomolecule. In one specific embodiment, the biomolecule is a protein. In another specific embodiment, the biomolecule is an antibody.

In one embodiment, the method of chemical modification comprises expressed protein ligation (EPL). In one preferred embodiment, the non-self cleaving Mxe GyrA intein may be linked to the C-terminus of the protein of interest. Specifically, the non-self cleaving Mxe GyrA intein may be linked by expressing the target protein with the intein linked to its C-terminus.

In one embodiment, Applicants envision that the present engineered Mxe GyrA intein may be expressed in any suitable medium as appreciated by one skilled in the art. For example, the present engineered Mxe GyrA intein may be expressed in bacteria, fungi or eukaryotic cells, such as mammalian cells.

In one embodiment, the present invention discloses an engineered intein for enhanced production of soluble fusion proteins in a microorganism, wherein the engineered Mxe GyrA intein is selected from the group consisting of clones 202-08, F2-02, and F5-06.

Kits for Using the Engineered Inteins

In one aspect, the present invention discloses a kit for using engineered inteins as discussed above for chemical modification of a protein.

In one embodiment, a kit for enhancing production of soluble fusion proteins with chemical modification, wherein the kit comprises at least one engineered intein, and wherein the intein improves both the display and the secretion levels of the fusion proteins in yeasts as compared with the wild type intein.

In one specific embodiment, the engineered intein in the kit may improve the fusion proteins display level at least by 1.4 fold and improve the fusion proteins secretion level at least by 4.4 fold in yeasts as compared with the wild type intein.

In one embodiment, the intein in the kit may be a non-self-cleaving Mxe GyrA intein. Specifically, the intein in the kit is selected from the group consisting of clone 202-08 (SEQ ID NOs:3 and 4), clone F2-02 (SEQ ID NOs:5 and 6), clone F5-06 (SEQ ID NOs:7 and 8) and expression products thereof.

In another embodiment, the intein in the kit is selected from the group consisting of clones 202-03, 202-08, 202-12, 202-13, 505-05, 505-11, F2-02, F5-06 and expression products thereof.

In another embodiment, the intein in the kit is selected from the group consisting of clones 202-03, 202-08, 202-12, 202-13, 505-05, 505-11, F1-01, F1-12, F1-16, F2-02, F2-05, F2-08, F2-18, F5-03, F5-06 and expression products thereof.

In another embodiment of the kit, the intein is configured to create a fusion protein.

In another embodiment of the kit, a nucleophile capable of excising the intein is added to the kit. Preferable nucleophiles include sulfur nucleophiles or nitrogen nucleophiles. In one preferred embodiment, the sulfur nucleophile may be MESNA or DTT. In another preferred embodiment, the nitrogen nucleophile may be a hydrazine.

In one embodiment, the present invention discloses a kit for enhancing production of soluble fusion proteins in a microorganism or eukaryotic cell host. The kit would include an engineered intein of the present invention and, optionally, a nucleophile. The kit preferably comprises at least one engineered Mxe GyrA intein selected from the group consisting of clone 202-08 (SEQ ID NOs:3 and 4), clone F2-02 (SEQ ID NOs:5 and 6), and clone F5-06 (SEQ ID NOs:7 and 8) and expression products thereof.

The Methods

In one aspect, the present invention discloses a method for chemically functionalizing a protein, preferably in a yeast host. In one embodiment, the method comprises the steps of (a) obtaining an engineered intein, wherein the intein is a non-self-cleaving engineered Mxe GyrA intein; (b) expressing the protein of interest as a fusion partner with the engineered intein in the host to form an intein-protein complex; and (c) adding a first compound having a nucleophile and a functional group into the complex, wherein the nucleophile of the compound reacts with the complex to release the protein from the complex, wherein the protein is then chemically linked to the functional group.

In one embodiment, the yeast is *Saccharomyces cerevisiae*.

In one embodiment, the protein is chemically functionalized via expressed protein ligation (EPL).

In one embodiment, the engineered Mxe GyrA intein improves a fusion protein display level at least by 1.4 fold and improves the fusion protein secretion level at least by 4.4 fold as compared with the wild type intein.

In one embodiment, the engineered intein is selected from the group consisting of engineered Mxe GyrA intein clone 202-08 (SEQ ID NOs:3 and 4), clone F2-02 (SEQ ID NOs:5 and 6), and clone F5-06 (SEQ ID NOs:7 and 8) and expression products thereof.

In one embodiment, the intein-protein complex in step (b) is further purified.

In one embodiment, the first compound is 2-mercapthoethanesulfonic acid (MESNA).

Any engineered intein as provided in the present application may be used for the present method. The engineered intein may be produced through any suitable method as understood by one skilled in the art.

In one specific embodiment, the engineered intein is a non-self-cleaving intein. In one embodiment, the non-self-cleaving intein is an engineered Mxe GyrA intein.

In one specific embodiment, the engineered Mxe GyrA intein is selected from the group consisting of engineered Mxe GyrA intein clone 202-08 (SEQ ID NOs:3 and 4), clone F2-02 (SEQ ID NOs:5 and 6), and clone F5-06 (SEQ ID NOs:7 and 8) and expression products thereof.

In another specific embodiment, the engineered Mxe GyrA intein is selected from the group consisting of clones 202-03, 202-08, 202-12, 202-13, 505-05, 505-11, F2-02, F5-06 and expression products thereof.

In another specific embodiment, the engineered Mxe GyrA intein is selected from the group consisting of clones 202-03, 202-08, 202-12, 202-13, 505-05, 505-11, F1-01, F1-12, F1-16, F2-02, F2-05, F2-08, F2-18, F5-03, F5-06 and expression products thereof.

Applicants envision that the engineered Mxe GyrA intein may also include inteins that have mutations at the same locations as the above clones but have different amino acids substitutions from the above clones. In one preferred embodiment, the amino acids may all have the same charge.

In one embodiment, the engineered Mxe GyrA intein is obtained by a method of directed evolution. Example 1 demonstrates the present engineered Mxe GyrA inteins can be produced through directed evolution.

In one embodiment, after the engineered intein is obtained, a protein is expressed as a fusion partner with the engineered intein in a host, such as a yeast, to form an intein-protein complex. In one specific embodiment, the protein is an antibody, and the complex is a fusion protein.

Applicants envision that any suitable construct as understood by one skilled in the art may be used for the expression process. In one specific embodiment, one construct suitable for display and purification of the resulting fusion protein may be chosen for the expression process.

Figure 1B:
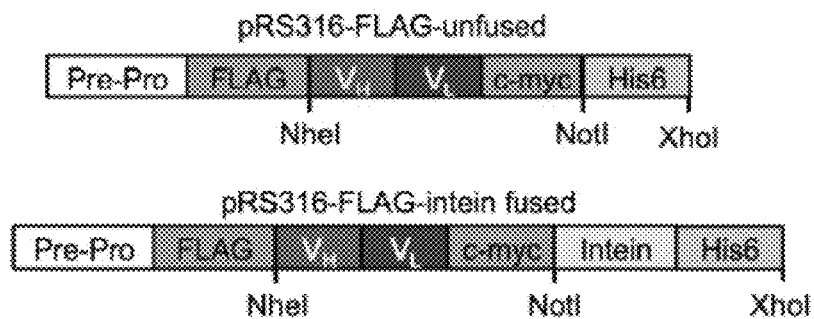

For example, in display construct pCT4Re, Aga2p may be expressed at the carboxy-terminus to anchor the fusion protein to the yeast surface, while a FLAG epitope tag is expressed on the amino-terminus of the scFv or GFP to indicate full-length construct expression on the yeast surface. In the intein-containing display constructs, the Mxe GyrA intein may be inserted between the carboxy-terminus of the scFv or GFP and the Aga2p surface anchor. Construct pRS316-FLAG may be used for secretion, with a synthetic pre-pro leader sequence directing secretion and a six histidine epitope for purification. FIGS. 1a and 1b are diagrams showing the structures of these surface display and secretion constructs.

After the formation of an intein-protein complex (e.g., a fusion protein), one would wish to remove the intein and add functional groups to the protein. In one embodiment, a nucleophile or nucleophiles may be used to remove the intein from the complex wherein the nucleophile or nucleophiles substitute the intein through a nucleophile substitution reaction. In one preferred embodiment, the nucleophile or nucleophiles may include sulfur or nitrogen nucleophiles. The remaining protein may be functionalized by chemically linking the protein to functional groups. In one embodiment, the nucleophile substitution reaction and the functionalization are a one-step reaction. For example, one can use a compound comprising both a nucleophile and a functional group to remove intein and add functional groups to the protein in one-step reaction.

In one specific embodiment, when nitrogen nucleophiles are used, one would expect a one-step reaction for removing intein and functionalizing the protein. In another specific embodiment, when sulfur nucleophiles are used, one would expect at least a two-step reaction for removing the intein and functionalizing the protein.

In one embodiment, one typical reaction for the present invention may be click chemistry reactions or EPL.

In one embodiment, the present invention discloses a method for chemically functionalizing a protein in a yeast. The method comprises the steps of (a) obtaining an engineered intein; (b) expressing the protein as a fusion partner with the engineered intein in the yeast to form an intein-protein complex; and (c) adding a compound having a nucleophile and a functional group into the complex, wherein the nucleophile of the compound reacts with the complex to release the protein from the complex, wherein the protein is chemically linked to the functional group.

In one embodiment, a first compound having a first nucleophile and a first leaving group may be added into the complex, wherein the first nucleophile of the first compound reacts with the complex to release the protein from the complex, wherein the protein is chemically linked to the first leaving group.

Applicants envision that any compound having at least one nucleophile and one leaving group may be used as the first compound.

In one embodiment, the first nucleophile may be a sulfur nucleophile or a nitrogen nucleophile.

In one embodiment, the first nucleophile is a sulfur nucleophile. The examples of the sulfur nucleophile may include thiols (RSH), thiolate anions (RS$^-$), anions of thiolcarboxylic acids (RC(O)—S$^-$), anions of dithiocarbonates (RO—C(S)—S$^-$), dithiocarbamates (R$_2$N—C(S)—S$^-$), and any other sulfur nucleophile as understood by one skilled in the art. In one preferred embodiment, the sulfur nucleophile may be MESNA or DTT.

In one embodiment, the first nucleophile is a nitrogen nucleophile. The examples of the nitrogen nucleophile may include ammonia, azide, amines, hydrazines, nitrites, and any other nitrogen nucleophile as understood by one skilled in the art. In one preferred embodiment, the nitrogen nucleophile may be a hydrazine or an amine.

In one embodiment, the first leaving group may be any suitable leaving group as appreciated by one skilled in the art. In one specific embodiment, the first leaving may include sulfonate or sulfonate esters, carboxylates, N-hydroxysuccinimide, N-hydroxybenzotriazole, halogen (halides), triflates, tosylates, mesylates, alkoxy, thioalkoxy, phosphinates, phosphonates, dinitrogen, dialkyl ether, perfluoroalkylsulfonates, mesylates or similar, nitrate, phosphate, sulfonate, thiolate, amine, amides, hydroxide, alkoxides, water, alcohols or others.

In one preferred embodiment, when EPL with MESNA is used in the present invention, the leaving group is a sulfonate.

In one specific embodiment, the first leaving group is a sulfonate or a sulfonate ester.

Figure 3B:
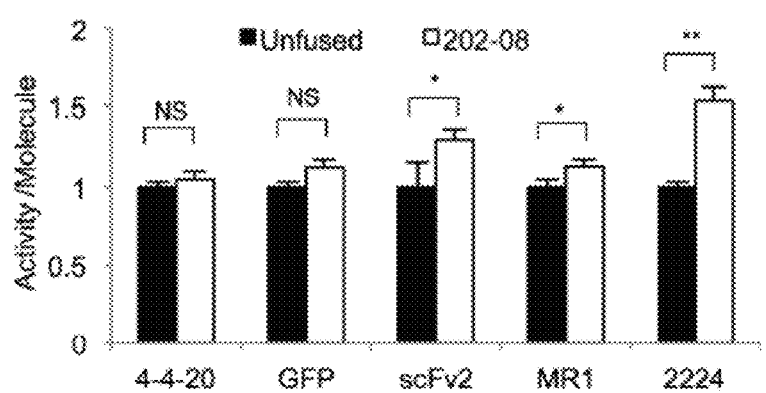
Figure 3C:
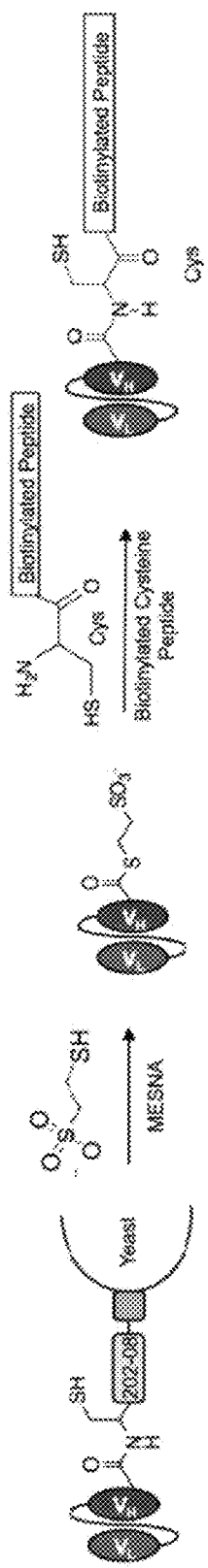

In one preferred embodiment, the first compound is 2-mercaptoethanesulfonic acid (MESNA). FIG. 3c shows the reaction of a clone 202-08 fusion protein with MESNA to release the protein from the fusion protein.

The other exemplary first compounds may include DTT or thiophenols.

As shown in FIG. 3c, after the reaction between the first compound and the complex, the protein is chemically linked to the first leaving group. Such chemical structure of the protein allows further chemical modification of the protein.

For example, the protein chemically linked to the first leaving group may react with a second compound having a second nucleophile and a functional group to form the protein chemically functionalized with the functional groups. The exemplary reaction for this step is expressed protein ligation (EPL).

In one embodiment, the non-self cleaving Mxe GyrA intein may be fused to the C-terminus of the protein of interest. It would be the same configuration as that used in display or secretion and the EPL component simply comes downstream after MESNA mediated release of the fusion protein from the intein. Specifically, the intein may be linked by expressing it as a fusion to the target protein. For example, a DNA plasmid was constructed and transformed into yeast. It encodes for the expression of the target protein as a fusion to intein. FIG. 1 shows a systematic scheme of the reaction.

In one embodiment, the second nucleophile may be a sulfur nucleophile, a nitrogen nucleophile, an oxygen nucleophile, a phosphorus nucleophile, or a selenium nucleophile as discussed above.

Figure 5A:
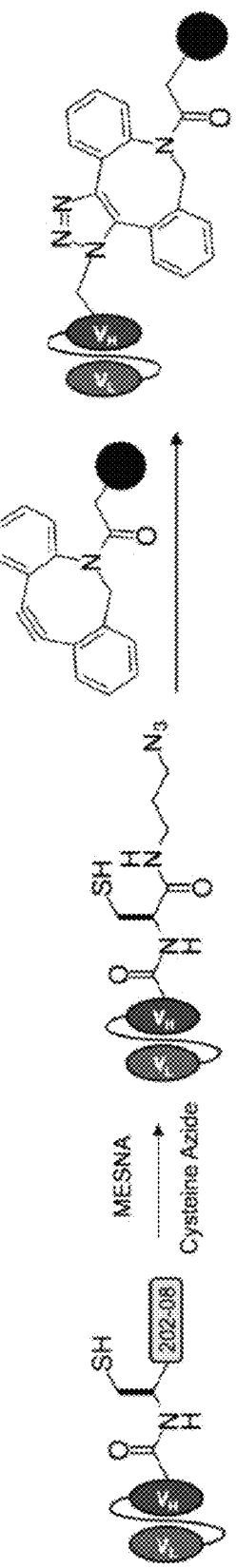
FIGS. 5a, 5b, 5c, and 5d are diagrams, pictures and graphs showing strain-promoted click chemistry immobilization.

In one specific embodiment, the second nucleophile may be a sulfur nucleophile or a nitrogen nucleophile. In a preferred embodiment, the second nucleophile is a nitrogen nucleophile. The exemplary nitrogen nucleophiles may include amine or azide. FIG. 3c shows an example using an amine as a nitrogen nucleophile. FIG. 5a shows an example using an azide as a nitrogen nucleophile.

In one embodiment, the functional group in the second compound may include any chemical functional group as appreciated by one skilled in the art. For example, one would use reactive functional groups, such as amine, thiol or azide for further functionalization.

In another embodiment, one would also use a biomolecule, e.g., a peptide, as the functional group to functionalize a protein. FIG. 3c shows an example using a peptide to functionalize a protein.

In one embodiment of the present invention, one-step reaction may be necessary for functionalizing a protein. For example, when a nitrogen nucleophile is used, the nitrogen nucleophile may be the first/only nucleophile in the one-step reaction scheme. For the thiol-based cleavage reaction, the second nucleophile may be required, which is also typically a sulfur nucleophile.

In one embodiment, the present method may include additional purification steps. Any method for purifying a protein may be used for the present invention. For example, Applicants envision that any preparative or analytical protein purifications may be used for the present invention.

A suitable analytical purification may utilize three properties to separate proteins. First, proteins may be purified according to their isoelectric points by running them through a pH gradient gel or an ion exchange column. Second, proteins can be separated according to their size or molecular weight via size exclusion chromatography or by SDS-PAGE (sodium dodecyl sulfate-polyacrylamide gel electrophoresis) analysis. Proteins are often purified by using 2D-PAGE and are then analyzed by peptide mass fingerprinting to establish the protein identity. Third, proteins may be separated by polarity/hydrophobicity via high performance liquid chromatography or reversed-phase chromatography.

Alternatively, proteins may also be purified and separated based on charge or hydrophobicity. Suitable methods may include Ion exchange chromatography, affinity chromatography, metal binding (e.g., polyhistidine-tag), immunoaffinity chromatography, or purification of a tagged protein.

In one embodiment, another suitable purification method may be a simultaneous MESNA/EPL reaction with purification on-resin cleavage. Kalia and Raines describe other purification methods suitable for the present invention (Kalia and Raines, 2006).

Example 1 demonstrates an exemplary method and process for chemically modifying a protein.

In one embodiment, the present invention discloses a method for chemically functionalizing a protein of interest in a microorganism or eukaryotic host cell. The method comprises the steps of (a) obtaining an engineered Mxe GyrA intein selected from the group consisting of clone 202-08 (SEQ ID NOs:3 and 4), clone F2-02 (SEQ ID NOs:5 and 6), and clone F5-06 (SEQ ID NOs:7 and 8) and expression products thereof; (b) expressing the protein of interest as a fusion partner with the engineered Mxe GyrA intein to form an intein-protein complex; and (c) adding a first compound having a nucleophile and a functional group into the complex, wherein the nucleophile of the compound reacts with the complex to release the protein from the complex, wherein the protein is chemically linked to the functional group.

In one embodiment, the host is selected from the group consisting of bacterial, yeast, mammalian and fungal cells.

In one embodiment, the protein is chemically functionalized via expressed protein ligation (EPL).

In one embodiment, the intein-protein complex in step (b) is further purified.

In one embodiment, the first compound is 2-mercapthoethanesulfonic acid (MESNA).

The present invention has been described in terms of one or more preferred embodiments, and it should be appreciated that many equivalents, alternatives, variations, and modifications, aside from those expressly stated, are possible and within the scope of the invention.

EXAMPLES

Example 1

Engineered Non-Self Cleaving Mxe Gyra Intein

Expressing antibodies as fusions to the non-self cleaving Mxe GyrA intein enables site-specific, carboxy-terminal chemical modification of the antibodies by expressed protein ligation (EPL). Bacterial antibody-intein fusion protein expression platforms typically yield insoluble inclusion bodies that require refolding to obtain active antibody-intein fusion proteins. Previously, we demonstrated that it was possible to employ yeast surface display to express properly folded single-chain antibody (scFv)-intein fusions, therefore permitting the direct small-scale chemical functionalization of scFvs. Here, directed evolution of the Mxe GyrA intein was performed to improve both the display and secretion levels of scFv-intein fusion proteins from yeast. The engineered intein was shown to increase the yeast display levels of eight different scFvs by up to 3-fold. Additionally, scFv- and green fluorescent protein (GFP)-intein fusion proteins can be secreted from yeast, and while fusion of the scFvs to the wild-type intein resulted in low expression levels, the engineered intein increased scFv-intein production levels by up to 30-fold. The secreted scFv- and GFP-intein fusion proteins retained their respective binding and fluorescent activities, and upon intein release, EPL resulted in carboxy-terminal azide functionalization of the target proteins. The azide-functionalized scFvs and GFP were subsequently employed in a copper-free, strain-promoted click reaction to site-specifically immobilize the proteins on surfaces, and it was demonstrated that the functionalized, immobilized scFvs retained their antigen binding specificity. Taken together, the evolved yeast intein platform provides a robust alternative to bacterial intein expression systems.

Introduction

Therapeutic and biochemical properties of antibodies can be enhanced by custom chemical functionalization that enables modifications such as small molecule drug conjugation,[1,2] PEGylation,[3,4] and conjugation to nanoparticles.[2,3,5] Expressed protein ligation (EPL) is one common approach to chemically modify proteins in a site-specific manner. In EPL, the target protein is expressed as a fusion partner to a non-self cleaving intein such as Mxe GyrA.[6-9] Intein-mediated protein splicing is activated by the addition of a thiol nucleophile that releases the target protein from the intein while simultaneously producing a carboxy-terminal thioester intermediate on the target protein. Subsequently, this carboxy-terminal thioester can be reacted with an appropriately functionalized amino-terminal cysteine to covalently attach a desired moiety to the carboxy-terminus of the target protein.

Non-self cleaving intein fusion proteins are most often expressed in the cytoplasm of Escherichia coli.[7,9-15] One disadvantage of cytoplasmic expression is the formation of insoluble inclusion bodies that contain inactive intein-fusion proteins, therefore requiring solubilization of the inclusion bodies and refolding of the protein.[7,9,10,14-16] Glutathione redox buffers that are typically used to refold disulfide-containing proteins like antibodies can react with the thioester intermediate formed by the intein, thereby releasing it from the target protein and forming an unstable glutathione thioester on the carboxy-terminus of the target protein.[10] This unstable glutathione thioester can subsequently be hydrolyzed leading to loss of the thioester functionality.[7,10] Additionally, in vivo autocleavage of the intein has been observed during protein expression, resulting in up to 90% loss of the intein for some fusion proteins.[17,18] These factors have combined to hamper antibody-intein fusion protein production using bacteria.[6,7]

Yeasts provide a possible alternative to bacterial expression systems, given their eukaryotic quality control machinery. Recently, scFvs were displayed as fusions to the Mxe GyrA mini-intein on the surface of Saccharomyces cerevisiae.[8] Contrasting with bacterial protein-intein fusion platforms, yeast-displayed scFv-intein protein fusions were properly folded and capable of engaging their antigenic targets. However, surface display levels of the scFvs were reduced by ~40% when fused to intein compared to the unfused antibody. In addition, surface display of heterologous proteins is not ideally suited for protein production at a preparative scale since protein expression on the yeast surface is limited to ~100,000 display constructs per yeast,[19,20] producing on the order of 70 μg of scFv per liter of yeast culture,[8] whereas baseline scFv secretion in yeast is in the multi-mg per liter range.[21,22] The yeast display levels of scFv-intein proteins could potentially be improved via directed evolution, as has been previously reported for a variety of proteins.[23,24] Moreover, improvements in yeast display often translate to improvements in secretion titer.[25-27] While directed evolution approaches have been employed to engineer catalytic properties of inteins such as temperature, pH, and ligand dependence,[28-31] intein-fusion protein expression levels have not been a target for improvement.

Therefore, in the current study, we sought to improve the production of scFv-intein fusion proteins both as displayed and secreted proteins. Directed evolution of the Mxe GyrA intein was employed as an scFv-intein fusion, and the yeast surface display levels of scFv-intein fusion proteins were restored to that of the unfused scFv. Furthermore, we demonstrated that the engineered intein dramatically improves secretion of scFv-intein fusion proteins from yeast, and, since the secreted proteins are folded and active, the scFvs can be directly functionalized and site-specifically immobilized via EPL and click chemistry.

Materials and Methods

Yeast Strains and Plasmids

Saccharomyces cerevisiae strain EBY100[19] (MATa AGA1::GAL1-AGA1::URA3 ura3-52 trp1 leu2Δ1 his3Δ200 pep4::HIS3 prb1Δ1.6R can1 GAL) was used for surface display, and strain YVH10[32] (MATα PDI1::GAPDH-PDI1::LEU2 ura3-52 trp1 leu2Δ1 his3Δ200 pep4::HIS3 prb1Δ1.6R can1 GAL) was used for protein secretion. The unfused and intein-fused pCT4Re vectors[8] were used as a backbone for surface display of the scFvs (FIG. 1a). Constructs pCT4Re-4420, pCT4Re-4420-intein, pCT4Re-scFv2, pCT4Re-scFv2-intein, pCT4Re-GFP, and pCT4Re-GFP-intein were generated in a previous study.[8] Anti-epidermal growth factor receptor mutant vIII (EGFRvIII) scFv, MR1[33] (GenBank accession number U76382), was synthesized by IDT DNA Technologies and subcloned into the pCT4Re constructs to create pCT4Re-MR1 and pCT4Re-MR1-intein. An scFv that binds the external domain of EGFR, 2224,[34] was synthesized by Life Technologies based upon the sequence provided in patent US 20100009390 A1[35] and subcloned into the pCT4Re constructs to create pCT4Re-2224 and pCT4Re-2224-intein. RBE4 binding scFvs selected in a previous study[36] were subcloned into the pCT4Re vectors to generate pCT4Re-scFvA, pCT4Re-scFvA-intein, pCT4Re-scFvD, pCT4Re-scFvD-intein, pCT4Re-scFvH, pCT4Re-scFvH-intein, and pCT4Re-scFv4S21, and pCT4Re-scFv4S21-intein. The pRS316-FLAG vector was created for protein secretion by inserting the constructs shown in FIG. 1b into the pRS316-Gal vector[37] between the GAL1-10 promoter and alpha factor terminator sequences to create unfused and intein-fused pRS316-FLAG vectors. The scFvs were subcloned into the pRS316-FLAG vectors to create pRS316-FLAG-4420, pRS316-FLAG-4420-intein, pRS316-FLAG-scFv2, pRS316-FLAG-scFv2-intein, pRS316-FLAG-GFP, pRS316-FLAG-GFP-intein, pRS316-FLAG-MR1, pRS316-FLAG-MR1-intein, and pRS316-FLAG-2224, pRS316-FLAG-2224-intein.

Yeast Growth and Induction

Yeast were transformed using the LiAc/ssDNA/PEG method.[38] For surface display strain EBY100, transformants were selected on tryptophan and uracil deficient SD-CAA agar plates (20.0 g/L dextrose, 6.7 g/L yeast nitrogen base, 5.0 g/L casamino acids, 10.19 g/L Na$_2$HPO$_4$. 7H$_2$O, 8.56 g/L NaH$_2$PO$_4$. H$_2$O, 15 g/L agar). For secretion strain YVH10, transformants were selected on leucine and uracil deficient SD-2×SCAA+Trp agar plates (20 g/L dextrose, 6.7 g/L yeast nitrogen base, 10.19 g/L Na$_2$HPO$_4$. 7H$_2$O, 8.56 g/L NaH$_2$PO$_4$. H$_2$O, 15 g/L agar 190 mg/L Arg, 108 mg/L Met, 52 mg/L Tyr, 290 mg/L Ile, 440 mg/L Lys, 200 mg/L Phe, 1260 mg/L Glu, 400 mg/L Asp, 480 mg/L Val, 220 mg/L Thr, 130 mg/L Gly, and 40 mg/L Trp, lacking leucine and uracil).

EBY100 yeast were grown in SD-CAA medium (20.0 g/L dextrose, 6.7 g/L yeast nitrogen base, 5.0 g/L casamino acids, 10.19 g/L Na$_2$HPO$_4$. 7H$_2$O, 8.56 g/L NaH$_2$PO$_4$. H$_2$O) until a culture density OD$_{600\ nm}$=1.0 was reached.

Surface display was induced by replacing the media with an equivalent volume of SG-CAA (20 g/L galactose replacing dextrose) for 20 h at 20° C., 260 rpm. Yeast secretion strain YVH10 was grown in SD-2×SCAA+Trp (20 g/L dextrose, 6.7 g/L yeast nitrogen base, 10.19 g/L $Na_2HPO_4 \cdot 7H_2O$, 8.56 g/L $NaH_2PO_4 \cdot H_2O$, 190 mg/L Arg, 108 mg/L Met, 52 mg/L Tyr, 290 mg/L Ile, 440 mg/L Lys, 200 mg/L Phe, 1260 mg/L Glu, 400 mg/L Asp, 480 mg/L Val, 220 mg/L Thr, 130 mg/L Gly, and 40 mg/L Trp, lacking leucine and uracil) at 30° C., 260 rpm overnight. The following day, cultures were reset to an $OD_{600\,nm}$=0.1, and grown for 72 h at 30° C., 260 rpm. Yeast were induced by replacing the media with an equivalent volume of SG-2×SCAA+Trp (20 g/L galactose replacing dextrose) containing 0.1% w/v bovine serum albumin (BSA) and culturing the cells for 72 h at 20° C. and 260 rpm.

EGFR Cell Lines and Creation of Cell Lysates

A431 (ATCC) and U87-EGFRvIII (kindly provided by Dr. Donald O'Rourke and Dr. Gurpreet S. Kapoor, University of Pennsylvania, Department of Neurosurgery) cell lines were maintained in Dulbecco's Modified Eagle's Medium (DMEM, Life Technologies) supplemented with 10% HyClone™ Cosmic Calf Serum (Thermo-Fisher) and 1× antibiotic/antimycotic (PSA, Gibco) at 37° C. and 5% $CO_2$. To prepare for lysis, cells were grown to ~90% confluence in 75 $cm^2$ tissue culture-treated T-flasks and washed three times with PBS. Cells were lysed by the addition of ice-cold 1 mL lysis buffer, consisting of 1% v/v Triton X-100 (Thermo-Fisher), 2 mM EDTA, and 1× Complete Protease Inhibitor Cocktail (Roche). Cells were scraped from the flask using a cell scraper at 4° C. and collected into a microfuge tube. The lysed cells were rotated at 4° C. for 15 min and centrifuged for 30 min to remove insoluble cell debris. The clarified lysates were then used to label yeast or antibody-conjugated beads as described below.

Intein Library Construction

Mutagenesis of the Mxe GyrA for the initial library creation was performed by error-prone PCR[39] of the pCT4Re-4420-intein construct containing intein using the nucleotide analogs 2'-deoxy-p-nucleoside-5'-triphosphate and 8-oxo-2'-deoxyguanosine-5'-triphosphate (TriLink Biotech) and primers (4420-intein-F5'-CAGAACAAAAGCT-TATTTCTGAAGAAGACTTGGCGGCCGCCGGCTGC-ATC-3'-SEQ ID NO:9) and (4420-intein-R5'-GGTGGTG-GTGGTTCTGGTGGTGGTGGTTCTGGTGGTGGTGGT-TCTGGATC-3'-SEQ ID NO:10) that amplified the intein sequence but preserved the amino-terminal cysteine that is essential to protein splicing. The intein library was created by homologous recombination in EBY100 using the mutagenized intein PCR product and the NotI/AleIII linearized pCT4Re-4420-intein acceptor vector (FIG. 1a). The initial library size was determined to be 2.5×$10^7$ clones by colony count. Twelve random yeast colonies were sequenced to determine an average nucleotide mutation rate of ~1.7%.

The second intein library was created by shuffling the mutations of clones 202-03, 202-08, 202-12, 202-13, 505-05, and 505-11 through assembly of degenerate oligonucleotides.[40] DNA oligonucleotides spanning the Mxe GyrA sequence were designed to contain the nucleotide base pair mutations at a 25:75 mutant: wild-type ratio. The intein gene was assembled from the oligonucleotides as previously described,[41] and additional mutagenesis of the assembled gene was performed with error prone PCR. The library was created by homologous recombination as described above, and the initial library size was determined to be 3.2×$10^7$ clones by colony count. An average nucleotide mutation rate of 1.8% was determined by sequencing 22 of the yeast colonies.

Library Screening

The first intein library was screened via fluorescence activated cell sorting (FACS) in five rounds of enrichment. For the first round of FACS, 2×$10^8$ yeast from the initial library were labeled to detect FLAG tag expression using the flow cytometry procedure described below. Clones with the highest expression level (~5%) were selected using a Becton Dickinson FACSVANTAGE SE sorter (University of Wisconsin Comprehensive Cancer Center). Using yeast from the previous sort, rounds 2-4 were completed in a similar manner. For the fifth round, yeast clones exhibiting both high construct expression and 4-4-20 activity were selected by labeling for the FLAG tag and binding to FITC-dextran. From the second intein library, 1.5×$10^8$ cells were labeled to detect FLAG tag expression and FITC-dextran binding, and clones with the highest expression level and binding (5%) were selected. Four additional rounds of FACS were performed, each time enriching the pool from the previous sort for high expression and FITC-dextran binding.

Individual clones were isolated by plating the final library pools on selective media (SD-CAA) and selecting single colonies for characterization. Plasmids were recovered from the yeast with the ZymoPrep Yeast Plasmid Miniprep II Kit (Zymo Research), and clones were sequenced with the following primers: mxe4420seq_F (5'TCTGT-GAAAGGCAGATTCACCA3'-SEQ ID NO:11) and mxe4420seq_R (5'ACAAAGAGTACGGCGTCGATT3'-SEQ ID NO:12). Clones were re-transformed into parent strain EBY100 for subsequent analysis.

Flow Cytometry

To determine surface display expression levels, the following anti-FLAG immunolabeling steps were performed at 4° C. prior to flow cytometry analysis. Induced EBY100 yeast were incubated with an anti-FLAG rabbit polyclonal antibody (Sigma-Aldrich, diluted 1:500 in PBS containing 0.1% BSA, PBS-BSA) for 30 min and washed once with PBS-BSA. Secondary antibody labeling was performed by incubating with either anti-rabbit Alexa 488 (Life Technologies, diluted 1:500 PBS-BSA), anti-rabbit PE (Sigma-Aldrich, diluted 1:45 in PBS-BSA), or anti-rabbit allophycocyanin (APC) (Life Technologies, diluted 1:500 in PBS-BSA) for 30 min, followed by a final wash with PBS-BSA. To evaluate 4-4-20 binding activity, yeast were incubated with 10 µM fluorescein isothiocyanate-functionalized dextran in PBS-BSA (FITC-dextran, Sigma-Aldrich) for 30 min at 4° C. followed by washing once with PBS-BSA prior to flow cytometry analysis. Activity of surface-displayed scFv2 and 2224 was evaluated by incubating yeast with purified human EGFR isolated from A431 cells by immunoaffinity chromatography[42] (4 µg/mL in PBS-BSA) for 1 h at 4° C., followed by washing once with PBS-BSA. Yeast were next incubated with anti-EGFR mouse antibody cocktail Ab-12 (Lab Vision Corporation, diluted 1:200 in PBS-BSA) for 30 min, washed once with PBS-BSA, and labeled with anti-mouse PE (Sigma-Aldrich, diluted 1:40 in PBS-BSA) for 30 min followed by a final wash with PBS-BSA. Binding of MR1 to EGFRvIII was evaluated by yeast display immunoprecipitation (YDIP).[43] Yeast were incubated with undiluted U87-EGFRvIII lysates in PBS containing 1% v/v Triton-X-100 (PBS-TX) for 1 h at 4° C., followed by washing once with PBS-TX and anti-EGFR primary and secondary antibody labeling steps as performed for scFv2 and 2224. GFP activity was evaluated by measuring the GFP fluorescence of the yeast at 488 nm excitation. The yeast cell fluorescence was measured using a FACSCALIBUR flow cytometer (Becton Dickinson), and the geometric mean fluorescence intensities of the protein displaying populations were quantified with the FLOWJO software package to determine relative display levels and activities.

Protein Purification

Following YVH10 growth and induction at the 50-mL scale, the yeast supernatant containing the secreted proteins was separated from the yeast by centrifugation and dialyzed against Tris-buffered saline (TBS, 25 mM Tris, 150 mM NaCl, 2 mM KCl, pH 7.9). The purification column was loaded with 750 µl Ni-NTA agarose (Qiagen) and equilibrated with 10 mL of bind buffer (TBS with 5 mM imidazole) prior to loading the dialyzed yeast supernatant. The column was subsequently washed with 15 mL of bind buffer followed by 3 mL of wash buffer (TBS with 20 mM imidazole), and the proteins were eluted with 2 mL TBS containing 250 mM imidazole.

SDS-PAGE and Western Blotting

Protein samples were reduced and denatured by boiling in LDS sample buffer (Life Technologies) containing 1 mM 2-mercaptoethanol for 10 min prior to resolution on 4-12% Bis-Tris gels (Life Technologies). Under these conditions, no additional intein cleavage above that of the 20-h MESNA reaction is observed. Proteins were subsequently transferred to a nitrocellulose membrane for Western blot analysis. Detection of FLAG tagged proteins was performed by probing the membranes with anti-FLAG M2 mouse monoclonal antibody (Sigma-Aldrich, diluted 1:3000) followed by anti-mouse HRP conjugate (Sigma-Aldrich, diluted 1:2000). To detect biotinylated proteins, membranes were probed with anti-biotin mouse monoclonal antibody Ab-2 clone BTN.4 (Lab Vision Corporation, diluted 1:500) followed by anti-mouse HRP conjugate. Membranes were developed using Clarity™ Western ECL Substrate (Bio-Rad) and imaged with the ChemiDoc XRS+ system (Bio-Rad). Unsaturated band intensities were measured with the Image Lab Software (Bio-Rad) to quantify the relative protein amounts.

Fluorescein Quench Assay and GFP Activity

The $K_d$ value for secreted 4-4-20 and 4-4-20-202-08 was calculated by fluorescein quenching as previously described.[32,44] Yeast supernatants containing the soluble proteins were dialyzed against TBS prior to analysis. Fluorescein (Sigma-Aldrich) was added stepwise to 1 mL of the dialyzed supernatant, and the resulting fluorescence at 514 nm was monitored using a FLUOROMAX-3 Spectrofluorometer (Horiba) and an excitation wavelength of 492 nm. The fluorescence intensities were fitted to an equilibrium binding model to determine the concentration and $K_d$ of the 4-4-20 proteins.

Secreted GFP activity was determined by measuring the emission spectrum of purified samples at 488 nm excitation with the Fluoromax-3 Spectrofluorometer, and the area under the curve was calculated. Anti-FLAG quantitative Western blotting was performed to determine relative GFP expression levels, and the fluorescence intensity was divided by expression level to calculate specific activity.

Intein-Mediated Release and EPL

The ability to release the scFvs and GFP from the display construct in an intein-dependent manner was also evaluated as previously described.[8] Briefly, yeast displaying the intein-linked constructs were incubated with 50 mM 2-mercapthoethanesulfonic acid (MESNA, Sigma-Aldrich) in TBS for 45 min at room temperature to release a mixture of scFvs and scFv-intein-Aga2p fusion proteins. The yeast were subsequently removed from the reaction mixture by centrifugation, and the supernatant containing MESNA and the released proteins was allowed to react for 20 h to complete release of the scFvs from intein. The released proteins were subjected to anti-FLAG Western blot analysis. Expressed protein ligation (EPL) with a biotinylated cysteine peptide was also performed as previously described.[8] Following the 45 min reaction of the yeast with the MESNA solution, the released proteins were separated from the yeast by centrifugation and 1 mM Bio-P1 peptide was added (synthesized by the University of Wisconsin Biotechnology Center, Sequence: $NH_2$-CDPEK(Bt)DS-$CONH_2$). The combined release and EPL reaction was allowed to proceed for 20 h at room temperature, and the proteins were analyzed with an anti-biotin Western blot.

For release and functionalization of the secreted scFvs and GFP, 100 µl of 1 M MESNA was added to 900 µl of purified scFv- or GFP-intein (~5-300 mg fusion protein/L) and the reaction was allowed to proceed for 20 h at room temperature prior to anti-FLAG Western blot analysis. To generate azide-functionalized proteins, cysteine azide (Anaspec) was added to a final concentration of 5 mM during a combined 20-h release and EPL reaction. The proteins were subsequently dialyzed with TBS to remove unreacted cysteine azides prior to performing the immobilization reactions.

Protein Immobilization Via Strain-Promoted Click Chemistry

The following protein immobilization and incubation steps were performed at room temperature with gentle rotation. Dibenzocyclooctyne (DBCO)-functionalized agarose (10 µl, Click Chemistry Tools) was blocked with 500 µl DBCO blocking buffer (PBS with 2% w/v BSA and 1% Tween-20) for 1 h. The blocking buffer was removed, and 200 µl of the azide-modified proteins were added to the beads for 2 h. The beads were subsequently washed twice with PBS-BSA and once with DBCO blocking buffer. To evaluate 4-4-20 binding to fluorescein, the antibody-linked beads were incubated in 10 µM FITC-dextran in PBS-BSA for 30 min followed by washing three times with PBS-BSA. Activity of the EGFR scFv was assayed by incubating the antibody-linked agarose beads with 200 µl of undiluted A431 cell lysates or U87-EGFRvIII cell lysates for 1 h. The beads were washed twice with PBS-TX and once with DBCO blocking buffer before incubation with 200 µl anti-EGFR antibody cocktail Ab-12 (1:200 dilution in DBCO blocking buffer) for 30 min. The antibody-linked beads were subsequently washed twice with PBS-BSA and once with DBCO blocking buffer, followed by incubating with 200 µl anti-mouse Alexa 488 antibody (1:500 dilution in DBCO blocking buffer) for 30 min. The beads were washed three times with PBS-BSA. Beads were imaged with an Olympus IX70 fluorescence microscope, and the fluorescence intensities of the beads at 509 nm were measured using a Tecan Infinite M1000 fluorescent microplate reader with an excitation wavelength of 488 nm.

Results

Intein Library Generation and Screening

Figure 2B:
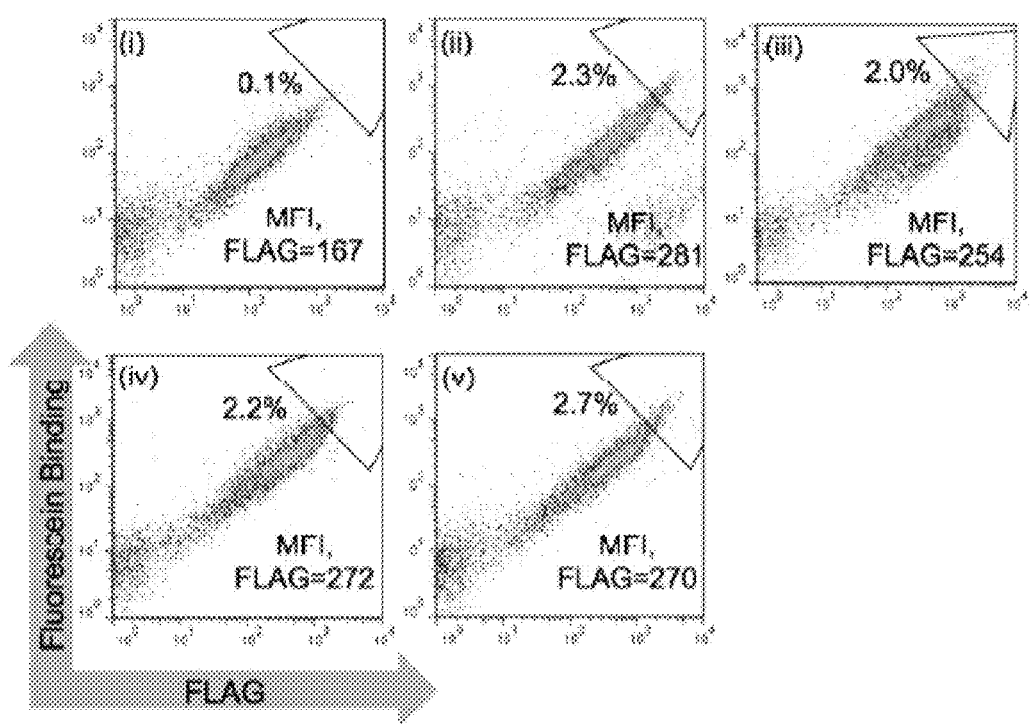

Evolution of the Mxe GyrA intein was performed with the primary screening criterion being increased yeast display of an scFv-intein fusion. The anti-fluorescein scFv (4-4-20) construct was employed as the fusion partner since intein fusion decreased yeast display by 40% compared with unfused 4-4-20 display,[8] offering a convenient screening pressure of improved yeast display (FIGS. 1a and 2a). For the first round of directed evolution, random mutagenesis was selectively targeted to the intein moiety, and upon recombination with unmutated 4-4-20, a library of ~2.5× $10^7$ 4-4-20-intein fusion mutants was generated. The library was enriched for clones with elevated full-length surface expression (FLAG epitope tag) through four rounds of fluorescence activated cell sorting (FACS), followed by one additional round of FACS that ensured retention of 4-4-20 binding activity by using fluorescein labeling in addition to FLAG epitope labeling (FIG. 2a). A 1.7-fold increase in display and fluorescein binding compared to the wild-type intein was observed in this final sorted pool (FIG. 2b, compare panels i and ii), and the display levels of the 4-4-20-intein fusion were restored to that of the unfused 4-4-20 protein (FIG. 2b, panel iv).

Individual intein clones were next isolated and evaluated for display levels and intein activity. Since mutations to the Mxe GyrA intein could potentially inhibit intein activity,[45] the clones were first screened for activity by examining 4-4-20 release from the 4-4-20-intein fusion construct by reaction with a sulfur nucleophile, MESNA. The wild-type intein catalyzes an N- to S-acyl shift at the amino-terminal cysteine of the intein, forming a thioester that is susceptible to a nucleophilic attack. Reaction with a nucleophile, such as MESNA, releases 4-4-20 from the intein and the yeast display construct while simultaneously appending a carboxy-terminal thioester onto 4-4-20 (FIG. 3c).[8] Because MESNA also reduces the disulfide bonds between Aga1p and Aga2p on the yeast surface (FIG. 2a),[8] 4-4-20 release from the intein could not be measured inline with the screen by flow cytometry. Instead, intein activity was determined for each individual clone via anti-FLAG Western blotting (shown in FIG. 2d for clone 202-08). Six mutated intein clones exhibited an increase in surface display over the wild-type intein and retained their cleavage activity (Table 1). In an attempt to further improve 4-4-20-intein fusion display levels, these six clones were shuffled and additionally mutated to create a library containing ~3.2×10^7 clones for a second round of directed evolution (see Materials and Methods for details).

TABLE 1

Intein mutations and surface display levels.

| Amino Acid | 21 | 33 | 50 | 51 | 74 | 105 | 107 | 110 | 112 | 114 | 117 | 118 | 124 | 129 | 144 | 158 | 160 | 164 | 168 | 190 | 191 | Fold Increase[a] | Statistical Significance[b] |
|---|---|---|---|---|---|---|---|---|---|---|---|---|---|---|---|---|---|---|---|---|---|---|---|
| Wild-Type | I | I | L | F | N | I | R | F | V | C | F | A | F | Y | H | D | R | A | S | I | T | 1.0 ± 0 | |
| 202-03 | | | | | | D | | | | | | | | | R | G | | | | | | 1.4 ± 1 | ** |
| 202-08 | | | L | | | | V | C | S | | | L | | L | | | | | G | | T | 1.8 ± 2 | ** |
| 202-12 | | T | P | | | | | | | A | C | | | | | | | | | | | 1.5 ± 3 | * |
| 202-13 | T | | | S | | | | | G | | | T | | | | | | Q | | | | 1.3 ± 2 | NS |
| 505-05 | T | | | | | | R | | | | | | | | | | | | | V | | 1.3 ± 1 | ** |
| 505-11 | | | | | | | | | | | | | C | | | | P | | | | M | 1.7 ± 1 | ** |

[a] Fold increase relative to the wild-type intein as fusions to 4-4-20, mean ± S.D from three independent yeast transformants.
[b] Statistical analysis was perfomed by an unpaired Student's t-test, with double asterisks representing p < 0.01, single asterisks representing p < 0.05, and NS designating that differences are not significant (p > 0.05).

Table 2 shows Intein mutations and the corresponding surface display levels and secretion levels.

TABLE 2

Intein mutations and the corresponding surface display levels and secretion levels.

| Amino Acid | 21 | 33 | 50 | 51 | 74 | 105 | 107 | 110 | 112 | 114 | 117 | 118 | 124 | 129 | 144 | 158 | 160 | 164 | 168 | 190 | 191 | Surface Display Fold Increase[a] | Statistical Significance[b] | Secretion Fold Increase[a] | Splicing[c] |
|---|---|---|---|---|---|---|---|---|---|---|---|---|---|---|---|---|---|---|---|---|---|---|---|---|---|
| Wild-Type | I | I | L | F | N | I | R | F | V | C | F | A | F | Y | H | D | R | A | S | I | T | 1.0 ± 0 | | | |
| 202-03 | | | | | | D | | | | | | | | | R | G | | | | | | 1.4 ± .1 | ** | 2.6 ± 1.3 | F |
| 202-08 | | | L | | | | V | C | S | | | L | | L | | | | | G | | T | 1.8 ± .2 | ** | 10.4 ± 1.4 | F |
| 202-12 | | T | P | | | | | | | A | C | | | | | | | | | | | 1.5 ± .3 | * | 0.5 ± .2 | P |
| 202-13 | T | | | S | | | | | G | | | T | | | | | | Q | | | | 1.3 ± .2 | NS | 1.9 ± .2 | F |
| 505-05 | T | | | | | | R | | | | | | | | | | | | | V | | 1.3 ± .1 | ** | 0.8 ± .6 | F |
| 505-11 | | | | | | | | | | | | | C | | | | P | | | | M | 1.7 ± .1 | ** | 1.1 ± .3 | F |
| F1-01 | | | | | | | A | | R | | T | | C | R | | | | | | | | 1.1 ± .1 | NS | 1.0 ± .3 | F |
| F1-12 | | T | | | D | | | | R | | | | | | | Q | | | | | | 1.8 ± .1 | ** | 1.0 ± .4 | P |
| F1-16 | | | S | | | | | | A | | | L | C | | | | | | | | M | 1.8 ± .3 | ** | 1.7 ± .3 | N |
| F2-02 | | | | | | | A | | R | T | | | R | | | G | | | | | | 1.4 ± .2 | NS | 6.5 ± 1.3 | F |
| F2-05 | T | | S | | | | | | G | L | | | | | Q | | | | | | | 1.8 ± .2 | ** | ND | P |
| F2-08 | | | S | | | | S | A | G | | T | | | | Q | | G | | | | | 1.4 ± .1 | * | 1.2 ± .7 | P |
| F5-03 | | | L | D | | | | S | | R | L | | L | | | | | | | | | 1.4 ± .1 | * | 6.3 ± .1.5 | P |
| F5-06 | | | | | C | S | | G | | T | | C | R | G | Q | | | | | | | 1.4 ± .3 | NS | 4.4 ± .1.4 | F |

[a] Fold increase relative to the wild-type intein as fusions to 4-4-20, mean ± S.D from three independent yeast transformants.
[b] Statistical analysis was perfomed by an unpaired Student's t-test, with double asterisks representing p < 0.01, single asterisks representing p < 0.05, and NS designating that differences are not significant (p > 0.05).
[c] Splicing capability of intein clones was determined by reacting yeast surface displayed intein fusion proteins with MESNA.
F: Full splicing;
P: partial splicing;
N: No splicing In the second round of evolution, the library was again screened for elevated display levels and fluorescein binding over five rounds of FACS. Characterization of the final pool demonstrated an increase in display levels compared to the wild-type intein, but display level was not significantly greater than that achieve through the first round of directed evolution (FIG. 2b, iii), as also confirmed by evaluation of individual clones (Table 3).

intein fusion reaching levels similar to or greater than that of the unfused protein (FIG. 3a). Next, the activity of GFP- and EGFR-specific scFv-intein fusions was evaluated to ensure the 202-08 intein did not have deleterious effects on the specific activity of its fusion partner. Much like the case of 4-4-20, GFP fluorescence activity was not altered by fusion with the 202-08 intein (FIG. 3b). Interestingly, compared with unfused scFv, fusion to 202-08 yielded small increases

TABLE 3

Intein mutations and surface display levels for directed evolution round 2.

| Amino Acid | 21 | 33 | 50 | 51 | 74 | 105 | 107 | 110 | 112 | 114 | 117 | 118 | 124 | 129 | 144 | 158 | 160 | 164 | 168 | 190 | 191 | Fold Increase[a] | Statistical Significance[b] |
|---|---|---|---|---|---|---|---|---|---|---|---|---|---|---|---|---|---|---|---|---|---|---|---|
| WT | I | I | L | F | N | I | R | F | V | C | F | A | F | Y | H | D | R | A | S | I | T | 1.00 ± .10 | |
| F1-01 | | | | | | | | | A | R | | T | | C | R | | | | | | | 1.11 ± .08 | NS |
| F1-12 | | T | | D | | | | | | R | | | | | | Q | | | | | | 1.75 ± .12 | ** |
| F1-16 | | | S | | | | | | A | | | | L | C | | | | | | | M | 1.78 ± .28 | ** |
| F2-02 | | | | | | | | | A | R | | T | | | R | | | | G | | | 1.39 ± .22 | NS |
| F2-05 | T | | S | | | | | | | G | L | | | | | Q | | | | | | 1.81 ± .05 | ** |
| F2-08 | | | S | | | | | S | A | G | | T | | | | Q | | | G | | | 1.42 ± .14 | * |
| F2-18 | | T | P | L | | | | | | H | L | T | | | | Q | | | | | | 1.53 ± .19 | * |
| F5-03 | | | L | | D | | | S | | R | L | | L | | | | | | | | | 1.36 ± .13 | * |
| F5-06 | | | | | | | C | S | | G | | T | | | C | R | G | Q | | | | 1.36 ± .33 | NS |

[a]Fold increase relative to the wild-type intein as fusions to 4-4-20, mean ± S.D from three independent yeast colonies.
[b]Statistical analysis was perfomed by an unpaired student's t-test, with double asterisks representing p < 0.01, single asterisks representing p < 0.05, and NS designating that differences are non-significant (p > 0.05).

Surface Display Characterization of the 202-08 Intein

Figure 2C:
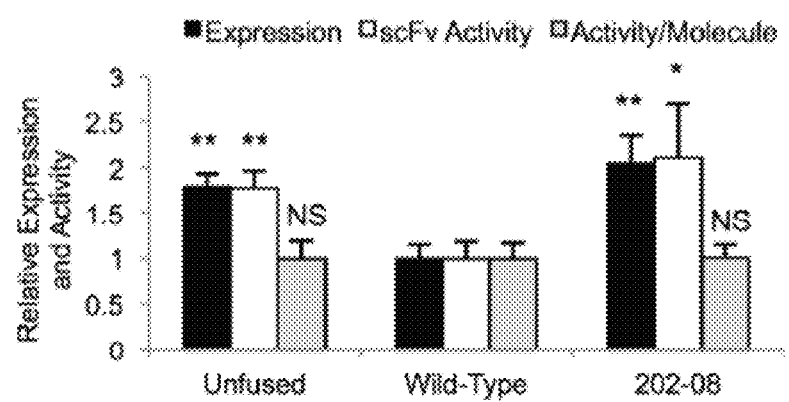
Figure 2D:
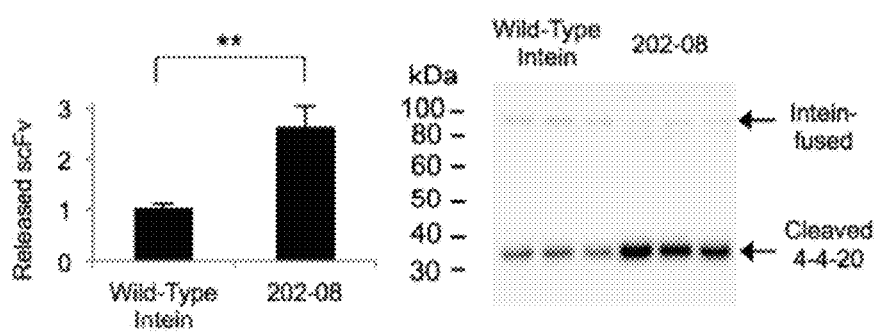
Figure 2E:
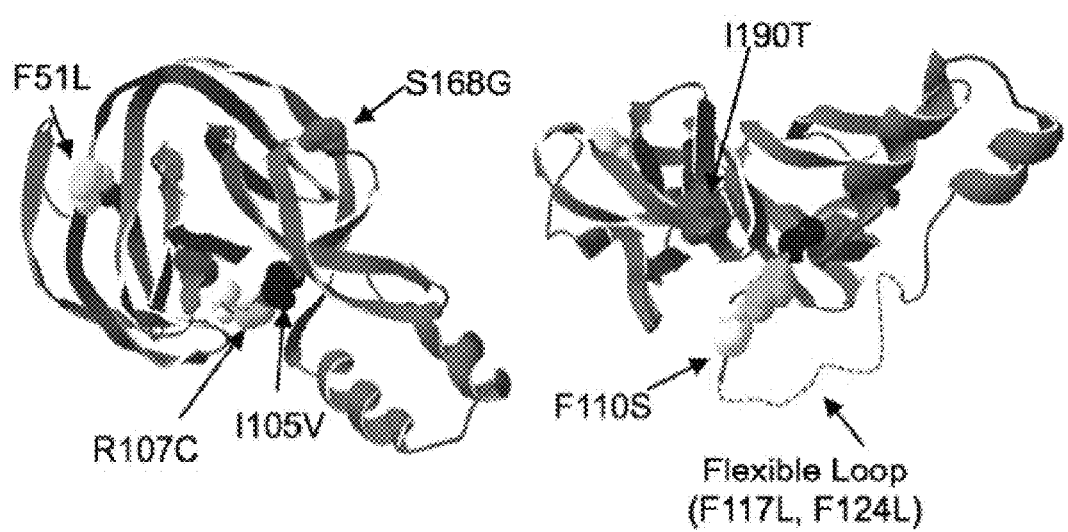

Clone 202-08 from round 1 of directed evolution was selected for further characterization based upon its elevated display levels, retention of protein splicing activity, and its capability to also significantly elevate secretion of scFv-intein fusions (discussed below). The 202-08 intein contained eight amino acid mutations (Table 1, FIG. 2e) and increased the surface display level of 4-4-20 1.8-fold compared to the wild-type intein fusion (FIG. 2b, v), making its display level comparable to that of the unfused 4-4-20 protein (FIG. 2c). Furthermore, the fluorescein binding per molecule of 4-4-20 was unchanged by fusion to 202-08 (FIG. 2c). The retention of 202-08 catalytic activity was confirmed by examining the relative amount of 4-4-20 cleaved from the yeast surface display construct in a MESNA release reaction. Quantitative Western blotting demonstrated a 2.6-fold increase in the amount of 4-4-20 released from yeast with clone 202-08 compared to the wild-type intein (FIG. 2d), consistent with the increased surface display levels mediated by the 202-08 intein (FIG. 2c).

Next, the generalizability of the 202-08 intein mutant was evaluated by testing effects on display and activity after its fusion to GFP and a cohort of 7 additional scFvs. The tested scFvs included three epidermal growth factor receptor (EGFR)-binding scFvs, scFv2,[46] MR1,[33] and 2224,[34,35] and a panel of brain endothelial-binding scFvs, scFvA, scFvD, scFvH, and 4S21[36] that collectively exhibit a range of unfused expression levels on the yeast surface (FIG. 3a). The expression level of GFP was unchanged upon fusion to wild-type intein as previously reported,[8] while scFv fusion to the wild-type intein generally decreased construct expression levels ~25-50%, regardless of unfused display efficiency (FIG. 3a). The lone exception was 2224, where both the unfused and wild-type intein-fused forms exhibited similar, low display levels (FIG. 3a). When each scFv or GFP was instead expressed as a fusion to the 202-08 intein, display was uniformly improved compared to the wild-type in per molecule EGFR binding for scFv2 and MR1, while 2224 exhibited more substantial 1.5-fold increases in binding to its EGFR ligand (FIG. 3b).

Protein Release and EPL for 202-08 Intein Fusions

Figure 3D:
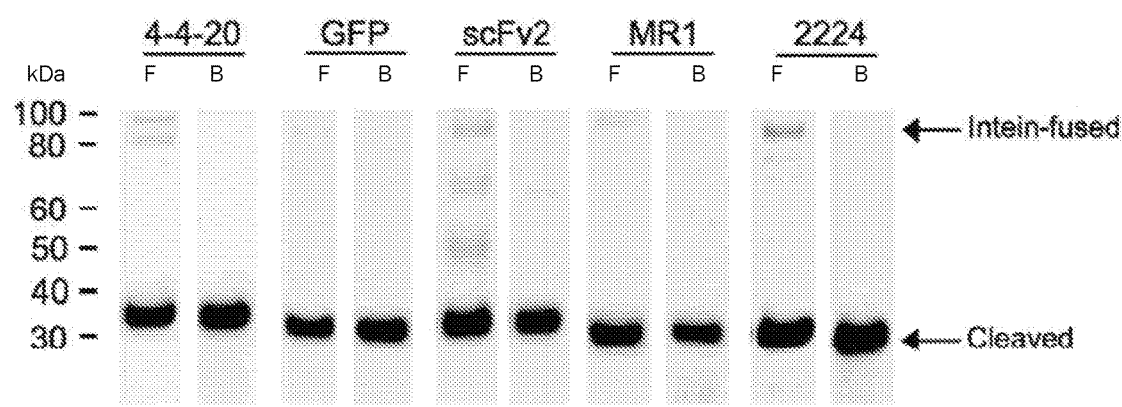
FIG. 3d: Products of the reaction depicted in panel c resolved and analyzed by Western blotting to detect release of the scFv or GFP (~30 kDa) from the 202-08 intein construct using an anti-FLAG antibody (F) or biotin functionalization via EPL with an anti-biotin antibody (B). A small amount of uncleaved scFv-intein-Aga2p product can be seen in the anti-FLAG Western blot between ~80 kDa and 100 kDa due to the glycosylation of Aga2p.

After demonstrating that intein clone 202-08 improved surface display of multiple scFvs and GFP, the intein cleavage activity was next confirmed. Yeast displaying 202-08 intein fusion proteins were reacted with MESNA to release the scFvs or GFP from the display construct, thereby generating scFv- and GFP-thioester proteins (FIG. 3c). Western blotting with an anti-FLAG antibody demonstrated nearly quantitative release of each of the scFvs and GFP from the 202-08 fusion display construct (FIG. 3d). The installation of the carboxy-terminal thioester functionality produced by intein-mediated release was confirmed by subjecting the MESNA-released scFvs and GFP to an EPL reaction with a biotinylated peptide possessing an amino-terminal cysteine (FIG. 3d). Anti-biotin Western blotting demonstrated successful biotinylation of the scFvs and GFP (FIG. 3d), indicating that the engineered 202-08 intein produces carboxy-terminal thioesters capable of EPL.

Secretion of scFv-Intein Fusion Proteins

Figure 4A:
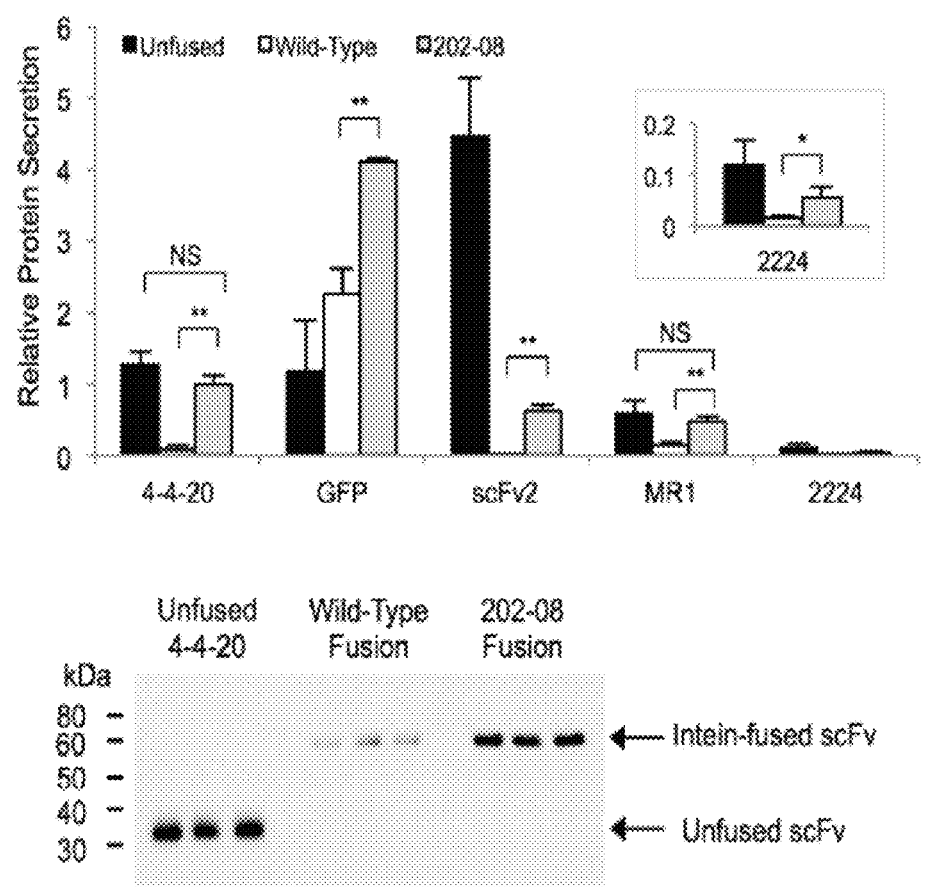
FIGS. 4a, 4b, 4c, and 4d are graphs and pictures showing secretion of scFv and GFP intein fusion proteins.

Next, yeast secretion constructs were designed to flank scFv or GFP inserts with the FLAG epitope tag at the amino-terminus and a six histidine epitope tag at the carboxy-terminus to permit protein detection (before or after intein release) and purification, respectively (FIG. 1b). Similar to the surface display experiments, secretion of unfused scFv or GFP was compared directly to the secretion of the same protein as a fusion to the amino-terminus of the wild-type or 202-08 intein (FIG. 1b). Along with GFP, four scFvs (4-4-20 and the EGFR-binding scFvs, scFv2, MR1, and 2224) were examined in the protein secretion studies. When the scFvs were produced as fusions to wild-type intein, quantitative Western blotting analysis demonstrated substantial decreases in scFv secretion, ranging from 75% (MR1) to 99% (scFv2) reduction compared to the unfused scFv, while GFP expression did not decrease when fused to wild-type intein (FIG. 4a). However, as observed with surface display, secreting the scFvs and GFP as fusions to the evolved 202-08 intein substantially improved the protein production compared to the wild-type intein fusion (FIG. 4a). Expression of MR1 and 4-4-20 increased 3- and 10-fold, respectively, compared to the wild-type intein fusion to achieve secretion levels that were comparable to the unfused protein (FIG. 4a). Fusion of 202-08 to scFv2 and 2224 increased secretion ~30-fold and ~3-fold over the wild-type intein fusions, respectively, although expression of these scFvs was not fully restored to the unfused protein level (FIG. 4a). Furthermore, even though the GFP fusion to the wild-type intein did not decrease secretion compared to the unfused GFP, expression when fused to 202-08 was modestly improved (~1.5 fold) over that of the wild-type intein (FIG. 4a).

Figure 4B:
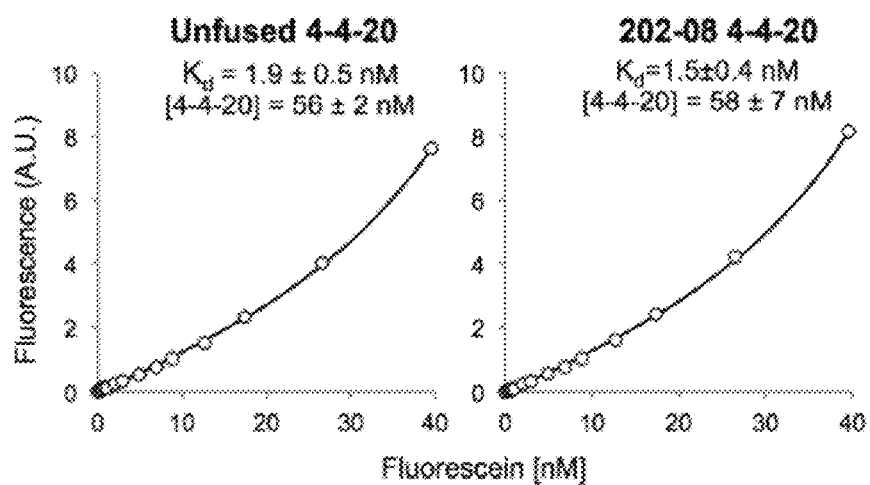
Figure 4C:
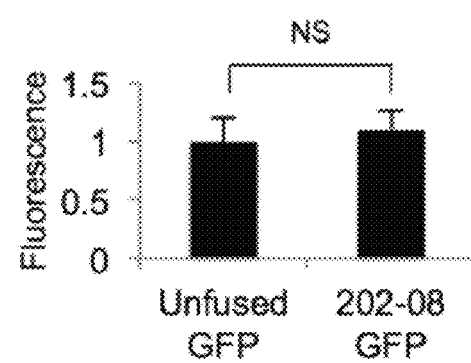
Figure 4D:
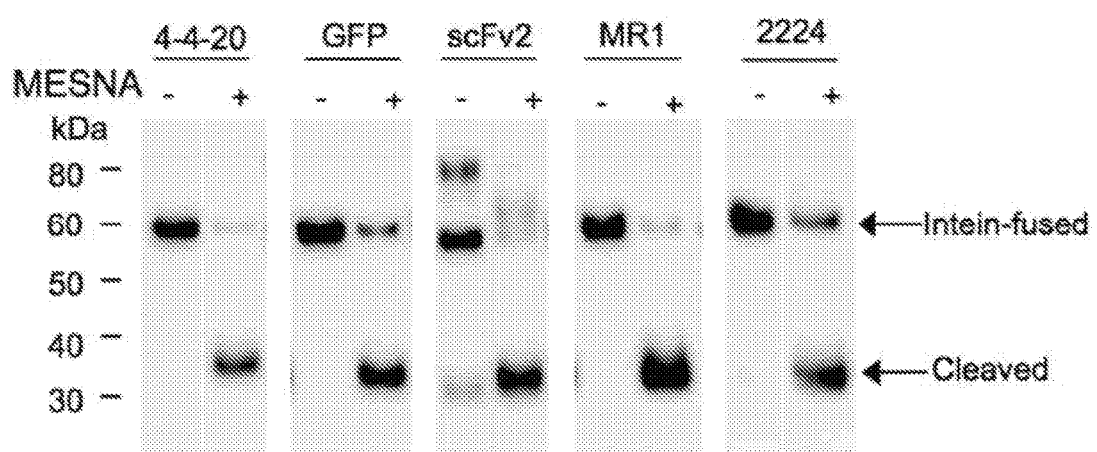
Figure 11:
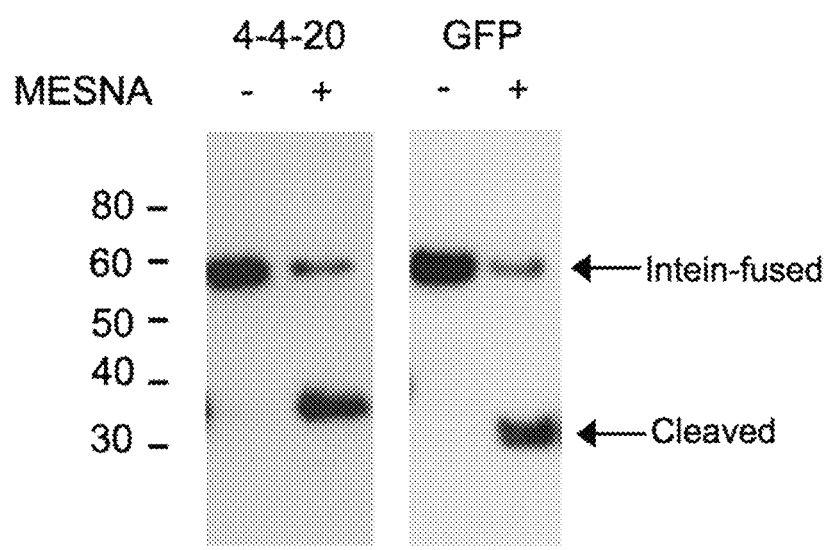
FIG. 11 shows MESNA release of 4-4-20 and GFP with the wild-type intein. The catalytic activity of the wild-type intein was examined by reacting secreted 4-4-20 and GFP with MESNA for 20 h. Anti-FLAG Western blotting demonstrates ~75% release for both 4-4-20 and GFP in the presence of MESNA.

Next, the activities of secreted scFv-intein fusion proteins were examined both from fusion partner and intein perspectives. First, 4-4-20 scFv and GFP activity was quantitatively evaluated using the secreted 4-4-20 and GFP intein fusion proteins (functionality of anti-EGFR scFvs evaluated as immobilized proteins below). The equilibrium binding affinity of 4-4-20 fused to 202-08 was measured in order to ensure that the antibody component of the fusion protein was folded and functional. Monitoring the fluorescence quench upon binding of fluorescein to 4-4-20 allowed determination of the equilibrium dissociation constant, $K_d$, of the 4-4-20-202-08 fusion protein to be 1.5±0.4 nM, making it statistically indistinguishable (p>0.05) from that of the unfused 4-4-20 protein (1.9±0.5 nM) (FIG. 4b). The activity of GFP fused to 202-08 was assessed by measuring its fluorescence per molecule and was shown to be identical to that of the unfused GFP (p>0.05) (FIG. 4c). Next, the intein-mediated release of the scFv or GFP from the 202-08 intein was evaluated by reacting the secreted and purified scFv or GFP fusion proteins with MESNA. All four scFvs along with GFP were released from the intein with efficiencies ranging from 70-99%, thus demonstrating that the 202-08 intein component is active when produced as a soluble fusion protein (FIG. 4d). Similar release efficiencies were observed for wild-type intein fusion proteins indicating that the engineered intein did not affect the cleaved scFv or GFP yields (FIG. 11).

Immobilization of scFv and GFP Via Strained Cycloaddition Reaction

Figure 5B:
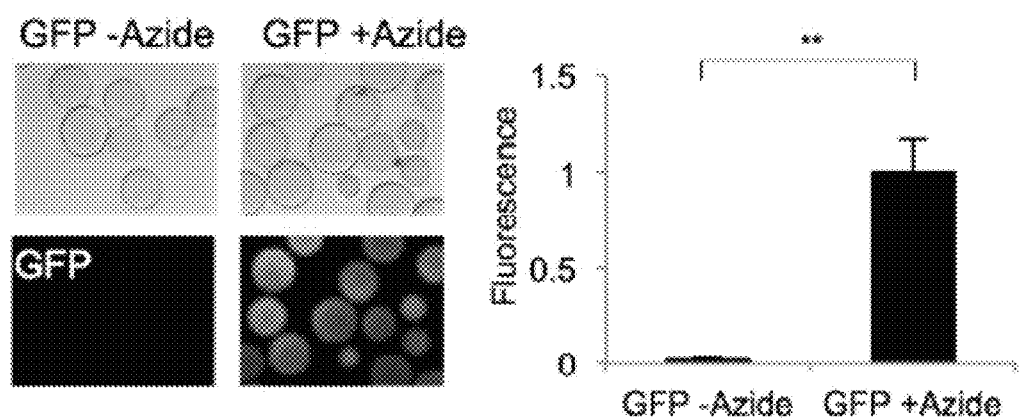
Figure 5C:
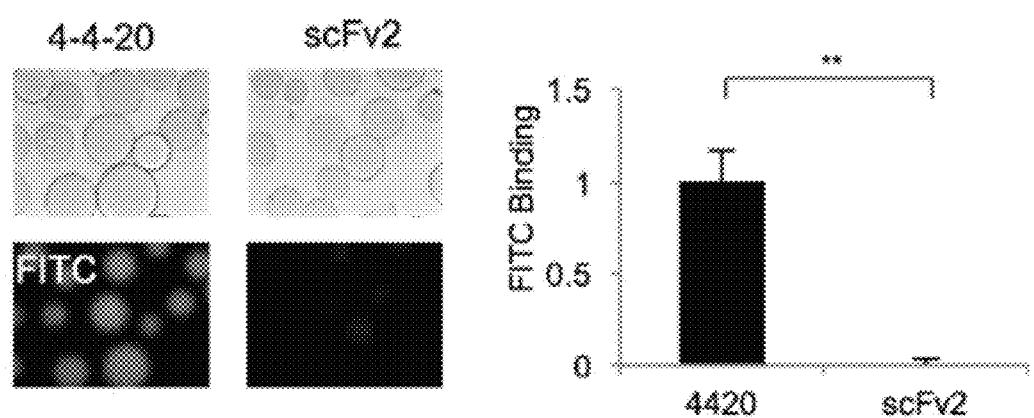
Figure 5D:
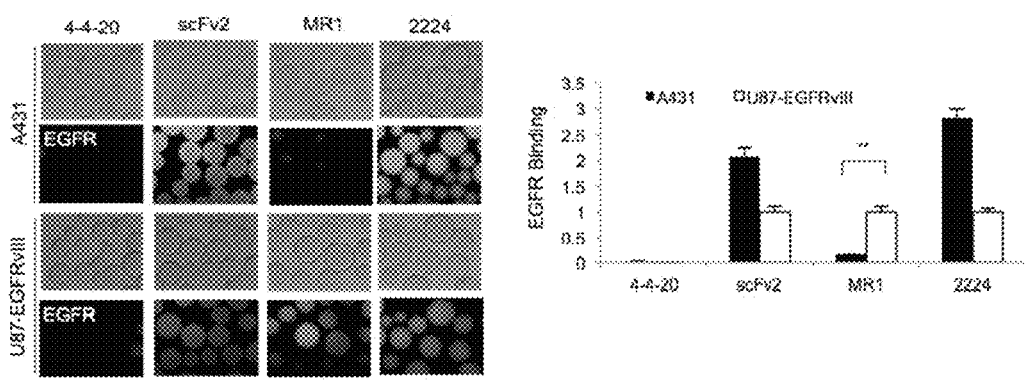
Figure 6:
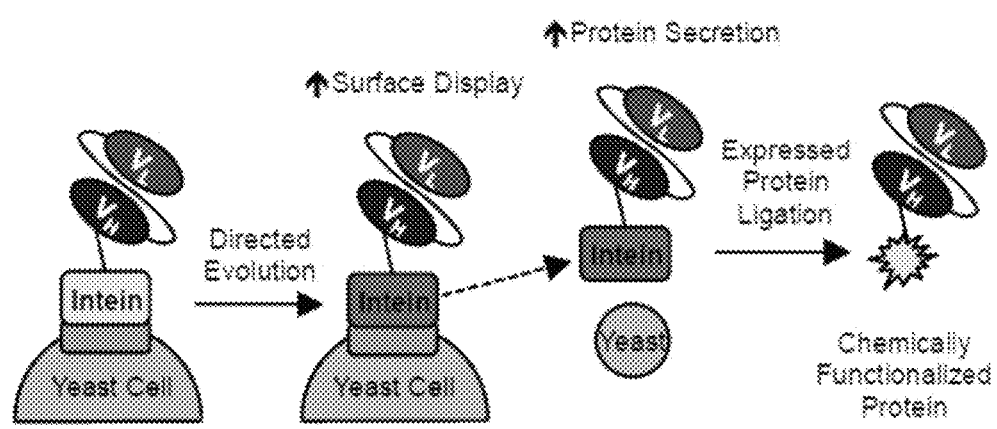
FIG. 6 is a diagram showing methods and processes for producing engineered inteins according to one embodiment of the present invention.

Next, by employing EPL functionalization techniques,[8,13] the scFvs and GFP were chemically functionalized to enable covalent immobilization of the proteins onto surfaces. The secreted and purified scFv- and GFP-202-08 intein fusion proteins were reacted with MESNA in the presence of cysteine azide, thereby releasing the scFv or GFP from the intein and installing a carboxy-terminal azide onto the protein (FIG. 5a). The azide-modified scFvs and GFP were subsequently reacted with dibenzocyclooctyne (DBCO)-functionalized agarose beads to immobilize the proteins via strain-promoted azide-alkyne cycloaddition (SPAAC) (FIG. 5a). In this way, GFP-azide protein was immobilized on the beads and yielded roughly 40-fold more GFP fluorescence than beads reacted with the control thioester functionalized GFP, indicating specific SPAAC-mediated immobilization of active GFP protein (FIG. 5b). Similarly, immobilization and activity of 4-4-20 was confirmed by specificity of fluorescein binding to beads loaded with 4-4-20-azide, but not EGFR-specific scFv2-azide (FIG. 5c). Finally, beads reacted with azide-functionalized EGFR scFvs were shown to bind their antigens from whole cell lysates that contained either wild-type EGFR or mutant EGFR vIII. ScFv2 and scFv2224 recognize epitopes conserved on both wild-type[34,35,46] and vIII EGFR isoforms,[34] while MR1 is a vIII-specific scFv.[33] Accordingly, if beads decorated with scFv2, 2224, or MR1 were incubated with cell lysates containing the EGFR vIII mutant, they all bound EGFR vIII as expected, while the anti-fluorescein 4-4-20 scFv exhibited negligible non-specific binding to the cell lysates (FIG. 5d). When incubated with wild-type EGFR-containing A431 cell lysates, beads loaded with scFv2-azide and 2224-azide again exhibited a clear binding signal. In contrast, beads loaded with MR1 exhibited a marked, 85% reduction in A431-derived EGFR binding signal compared to that generated from EGFR vIII cell lysates, indicating a clear preference for MR1 binding to the EGFR vIII mutant (FIG. 5d). Taken together, each of the scFvs retained antigen-specific binding activity after being produced as secreted protein-intein fusions, EPL reaction, and SPAAC immobilization.

Discussion

Producing antibodies as fusion partners to the Mxe GyrA intein enables site-specific, bioorthogonal chemical protein modification, thereby enabling antibody conjugation to desired small molecules, proteins, or surfaces. Through directed evolution, we have engineered the Mxe GyrA intein to increase the amount of scFv-intein fusion proteins displayed on the yeast surface by ~1.5- to 3-fold, thus increasing the amount of chemically functionalized protein obtained via intein-linked yeast surface display. Importantly, the engineered 202-08 intein clone was shown to be generalizable by increasing the surface display of GFP and eight different scFvs. Furthermore, we demonstrated that the engineered intein improves secretion of scFv-intein fusion proteins by ~3- to 30-fold over the wild-type intein. Finally, secreted scFvs could be directly modified via EPL, immobilized onto surfaces using SPAAC, and employed to bind their respective antigens.

While previous studies have employed rational design to improve Mxe GyrA production levels by reducing in vivo autocleavage[16,18] or by reducing intein size,[16] we instead employed directed evolution to achieve this goal. The surface display levels of scFv-intein fusions are generally 25-50% reduced compared to the unfused scFv, thus providing a screening pressure for improved intein clones. Although the screen employed intein fusion to the anti-fluorescein scFv, 4-4-20, intein clone 202-08 increased surface display of seven additional scFvs that exhibited a range of display levels as unfused proteins. For many different scFvs, 202-08 returned surface display of scFv-intein fusions back to unfused levels and this unfused display level appeared to be the ceiling for 4-4-20 expression, given the inability to achieve further expression increases in a second round of directed evolution. However, the display levels of two of the tested proteins, GFP and 2224, fused to the 202-08 intein did exceed that of the respective unfused proteins, and the 2224 scFv had an improved EGFR-specific binding capacity, indicating beneficial folding and processing effects of the intein fusion partner. These two proteins also did not demonstrate a decrease in expression upon fusion to the wild-type intein, and so the "chaperone-like" effects of the 202-08 may be limited to proteins that are better equipped to handle intein fusion. It has previously been reported that surface display levels often correlate with secretion levels,[21,25-27] and that modest elevation in surface display can lead to substantial increases in protein secretion.[47] Similarly, in this study, fairly modest display improvements produced by 202-08 resulted in substantial secretion improvements. For two of the scFvs, 4-4-20 and MR1, the 202-08 fusion increased expression 10- and 3-fold, respectively, to restore the secretion level to that of the unfused protein. Although unfused protein secretion levels were not restored for all of the tested scFvs, substantial increases in secretion were still obtained. As a result of 202-08 fusion, scFv production levels using the basal low-copy expression vector were estimated to range from 90 ug to 1.6 mg per liter of yeast culture for the antibodies tested here (6 mg/L for GFP), which is consistent with typical scFv yields in yeast,[22] and greatly improves upon that for wild-type intein fusions (30 to 250 μg/L). In addition, much like the 202-08 intein fusion yeast surface display levels, the 202-08 intein fusion secretion levels tend to track reasonably well with those of the unfused proteins, suggesting that the engineered intein has minimized the detrimental effects of intein fusion on protein secretion. Thus, the 202-08 intein should be generally compatible with fusion protein partners that are successfully produced in *Saccharomyces cerevisiae*.

Non-self cleaving intein fusion proteins have traditionally been expressed in the cytoplasm of *E. coli*, where they are often produced as insoluble inclusion bodies, thus requiring protein solubilization and refolding in order to obtain active protein.[7,10,14-16,18] In addition to requiring post-production processing to produce active intein-fusion proteins, the refolding process can result in thioester hydrolysis, thus preventing or substantially reducing subsequent EPL functionalization of the target protein.[7,10] One possibility to circumvent refolding issues in bacteria would be targeting of fusion proteins to the periplasm, where the oxidizing environment enables the formation of disulfide bonds and can potentially provide advantages for protein folding. This approach was successful with a single-domain antibody (sdAb) fused to the Mxe GyrA intein,[6] but has not yet been demonstrated for a broad panel of antibody fusion partners. In addition, since some antibodies are still expressed as unfolded aggregates in the periplasm,[48-50] while others simply cannot be expressed,[50,51] periplasmic expression of antibody-intein fusions may have limitations. Thus, as an alternative, expressing scFv-intein fusion proteins in a eukaryotic organism such as yeast could be beneficial. Indeed, by employing the evolved 202-08 intein, a panel of active scFv- and GFP-intein fusion proteins could be displayed or secreted from yeast and directly functionalized via EPL without any solubilization or refolding steps. In addition, expression levels in yeast and bacteria are often quite similar when comparing the same scFvs,[52] and 202-08 intein fusion expression levels for the more well-expressed scFvs tested were similar to the reported ~2-5 mg/L levels for scFv- and sdAb-intein fusion proteins using bacteria.[6,7] Thus, the yeast-based 202-08 intein system, with its combination of reasonable fusion protein yields and proper fusion protein folding, represents a competitive alternative to bacterial intein expression systems.

While we observed near complete release of the scFv or GFP with surface displayed intein fusion proteins, the secreted protein cleavage efficiencies ranged from 70-99% depending upon the fusion partner. The evolved 202-08 intein did not appear to affect cleavage efficiency compared with the wild-type intein, and these cleavage efficiencies are consistent with those observed for bacterially produced proteins.[7,16,53] Furthermore, the release could possibly be enhanced by optimizing the carboxy-terminal residue of the target protein, which has previously been shown to impact the cleavage efficiency.[53,54] Regardless, the small amount of uncleaved material is not chemically functionalized and would not impact many downstream applications like antibody immobilization, but the uncleaved material could be removed by depletion via histidine tag purification if desired.

The directed evolution process revealed that several different combinations of mutations led to improvements in scFv-intein surface display levels, and that no single mutation dominated either round of directed evolution (Table 1 and Table 3). A large percentage of the mutations (44%) found in the round 1 clones were within or in close proximity to the flexible loop of the Mxe GyrA intein that could not be resolved by crystallography (residues 112-129). Specifically, for 202-08, two of its eight mutations (F117L, F124L) fell within the flexible loop, while three other mutations occurred near the amino-terminus of the loop (I105V, R107C, F110S) (FIG. 2c). Thus, it appears that modifications in and around the flexible loop may be key to improving fusion protein expression. This finding is also supported by a recent study where a smaller Mxe GyrA intein was created by deleting residues 107-160 (including the flexible loop) and replacing the deletion with a short glycine-serine linker. This smaller intein variant led to a 1.2-fold increase in intein-peptide fusion production in *E. coli*.[16]

The secreted, EPL-functionalized scFvs and GFP were shown to be compatible with strain-promoted click chemistry, thus demonstrating the utility of intein fusion protein production in yeast. A carboxy-terminal azide was installed via EPL, and using SPAAC, active scFv and GFP were site-specifically immobilized on beads decorated with a strained alkyne. Previously we had demonstrated the compatibility of yeast displayed scFv-intein fusions with one of the most widely used forms of click chemistry, copper(I)-catalyzed azide-alkyne cycloaddition (CuAAC).[8,55] CuAAC requires the addition of copper, a reducing reagent, and a stabilizing ligand. In contrast, SPAAC enables the direct immobilization of azide-conjugated proteins without a copper catalyst, reducing reagent, or stabilizing ligand. Not only does SPAAC simplify the conjugation process, but it also prevents issues associated with the copper catalyst, such as protein precipitation[12,56,57] and toxicity.[58,59] Thus, the ability to employ these scFvs in SPAAC reactions offers many potential applications such as the generation of antibody-drug conjugates[60,61] and targeted nanoparticles.[62,63] In conclusion, directed evolution of the Mxe GyrA intein has permitted the extension of EPL and click chemistry modification techniques to scFvs secreted from yeast, thereby providing a viable alternative to bacterial expression systems and a facile method to chemically functionalize antibodies and other proteins.

REFERENCES (1) Adams, G., Shaller, C., Chappell, L., Wu, C., Horak, E., Simmons, H., Litwin, S., Marks, J., Weiner, L., and Brechbiel, M. (2000) Delivery of the α-emitting radio-isotope bismuth-213 to solid tumors via single-chain Fv and diabody molecules, *Nuclear medicine and biology* 27, 339-346.

(2) Kuimova, M. K., Bhatti, M., Deonarain, M., Yahioglu, G., Levitt, J. A., Stamati, I., Suhling, K., and Phillips, D. (2007) Fluorescence characterisation of multiply-loaded anti-HER2 single chain Fv-photosensitizer conjugates suitable for photodynamic therapy, *Photochemical & Photobiological Sciences* 6, 933-939.

(3) Nielsen, U. B., Kirpotin, D. B., Pickering, E. M., Hong, K., Park, J. W., Refaat Shalaby, M., Shao, Y., Benz, C. C., and Marks, J. D. (2002) Therapeutic efficacy of anti-ErbB2 immunoliposomes targeted by a phage antibody selected for cellular endocytosis, *Biochimica et Biophysica Acta (BBA)—Molecular Cell Research* 1591, 109-118.

(4) Natarajan, A., Xiong, C. Y., Albrecht, H., DeNardo, G. L., and DeNardo, S. J. (2005) Characterization of site-specific ScFv PEGylation for tumor-targeting pharmaceuticals, *Bioconjugate chemistry* 16, 113-121.

(5) Lu, R. M., Chang, Y. L., Chen, M. S., and Wu, H. C. (2011) Single chain anti-c-Met antibody conjugated nanoparticles for in vivo tumor-targeted imaging and drug delivery, *Biomaterials* 32, 3265-3274.

(6) Reulen, S. W., van Baal, I., Raats, J. M., and Merkx, M. (2009) Efficient, chemoselective synthesis of immunomicelles using single-domain antibodies with a C-terminal thioester, *BMC biotechnology* 9, 66.

(7) Sydor, J. R., Mariano, M., Sideris, S., and Nock, S. (2002) Establishment of Intein-Mediated Protein Ligation under Denaturing Conditions: C-Terminal Labeling of a Single-Chain Antibody for Biochip Screening, *Bioconjugate Chemistry* 13, 707-712.

(8) Marshall, C. J., Agarwal, N., Kalia, J., Grosskopf, V. A., McGrath, N. A., Abbott, N. L., Raines, R. T., and Shusta, E. V. (2013) Facile chemical functionalization of proteins through intein-linked yeast display, *Bioconjugate chemistry* 24, 1634-1644.

(9) Ayers, B., Blaschke, U. K., Camarero, J. A., Cotton, G. J., Holford, M., and Muir, T. W. (1999) Introduction of unnatural amino acids into proteins using expressed protein ligation, *Peptide Science* 51, 343-354.

(10) Bastings, M. M. C., Van Baal, I., Meijer, E., and Merkx, M. (2008) One-step refolding and purification of disulfide-containing proteins with a C-terminal MESNA thioester, *BMC Biotechnology* 8, 76.

(11) Elias, D. R., Cheng, Z., and Tsourkas, A. (2010) An Intein-Mediated Site-Specific Click Conjugation Strategy for Improved Tumor Targeting of Nanoparticle Systems, *Small* 6, 2460-2468.

(12) Kalia, J., and Raines, R. T. (2006) Reactivity of Intein Thioesters: Appending a Functional Group to a Protein, *Chem Bio Chem* 7, 1375-1383.

(13) Lin, P. C., Ueng, S. H., Tseng, M. C., Ko, J. L., Huang, K. T., Yu, S. C., Adak, A. K., Chen, Y. J., and Lin, C. C. (2006) Site-Specific Protein Modification through Cul-Catalyzed 1,2,3-Triazole Formation and Its Implementation in Protein Microarray Fabrication, *Angewandte Chemie* 118, 4392-4396.

(14) Valiyaveetil, F. I., MacKinnon, R., and Muir, T. W. (2002) Semisynthesis and Folding of the Potassium Channel KcsA, *Journal of the American Chemical Society* 124, 9113-9120.

(15) Guo, C., Li, Z., Shi, Y., Xu, M., Wise, J. G., Trommer, W. E., and Yuan, J. (2004) Intein-mediated fusion expression, high efficient refolding, and one-step purification of gelonin toxin, *Protein Expression and Purification* 37, 361-367.

(16) Albertsen, L., Shaw, A. C., Norrild, J. C., and Strømgaard, K. (2013) Recombinant production of peptide C-terminal α-amides using an engineered intein, *Bioconjugate chemistry* 24, 1883-1894.

(17) Wood, R. J., Pascoe, D. D., Brown, Z. K., Medlicott, E. M., Kriek, M., Neylon, C., and Roach, P. L. (2004) Optimized Conjugation of a Fluorescent Label to Proteins via Intein-Mediated Activation and Ligation, *Bioconjugate Chemistry* 15, 366-372.

(18) Cui, C., Zhao, W., Chen, J., Wang, J., and Li, Q. (2006) Elimination of in vivo cleavage between target protein and intein in the intein-mediated protein purification systems, *Protein expression and purification* 50, 74-81.

(19) Boder, E. T., and Wittrup, K. D. (1997) Yeast surface display for screening combinatorial polypeptide libraries, *Nature biotechnology* 15, 553-557.

(20) Chao, G., Lau, W. L., Hackel, B. J., Sazinsky, S. L., Lippow, S. M., and Wittrup, K. D. (2006) Isolating and engineering human antibodies using yeast surface display, *Nature protocols* 1, 755-768.

(21) Wentz, A. E., and Shusta, E. V. (2008) Enhanced Secretion of Heterologous Proteins from Yeast by Overexpression of Ribosomal Subunit RPP0, *Biotechnology Progress* 24, 748-756.

(22) Huang, D., and Shusta, E. V. (2006) A yeast platform for the production of single-chain antibody-green fluorescent protein fusions, *Applied and environmental microbiology* 72, 7748-7759.

(23) Shusta, E. V., Holler, P. D., Kieke, M. C., Kranz, D. M., and Wittrup, K. D. (2000) Directed evolution of a stable scaffold for T-cell receptor engineering, *Nature biotechnology* 18, 754-759.

(24) Starwalt, S. E., Masteller, E. L., Bluestone, J. A., and Kranz, D. M. (2003) Directed evolution of a single-chain class II MHC product by yeast display, *Protein Engineering Design and Selection* 16, 147-156.

(25) Shusta, E. V., Kieke, M. C., Parke, E., Kranz, D. M., and Wittrup, K. D. (1999) Yeast polypeptide fusion surface display levels predict thermal stability and soluble secretion efficiency, *Journal of molecular biology* 292, 949-956.

(26) Piatesi, A., Howland, S. W., Rakestraw, J. A., Renner, C., Robson, N., Cebon, J., Maraskovsky, E., Ritter, G., Old, L., and Wittrup, K. D. (2006) Directed evolution for improved secretion of cancer-testis antigen NY-ESO-1 from yeast, *Protein Expression and Purification* 48, 232-242.

(27) Rakestraw, J. A., Sazinsky, S. L., Piatesi, A., Antipov, E., and Wittrup, K. D. (2009) Directed evolution of a secretory leader for the improved expression of heterologous proteins and full-length antibodies in *Saccharomyces cerevisiae*, *Biotechnology and bioengineering* 103, 1192-1201.

(28) Adam, E., and Perler, F. B. (2002) Development of a positive genetic selection system for inhibition of protein splicing using mycobacterial inteins in *Escherichia coli* DNA gyrase subunit A, *Journal of molecular microbiology and biotechnology* 4, 479-488.

(29) Cann, I. K., Amaya, K. R., Southworth, M. W., and Perler, F. B. (2004) Bacteriophage-based genetic system for selection of nonsplicing inteins, *Applied and environmental microbiology* 70, 3158-3162.

(30) Zeidler, M. P., Tan, C., Bellaiche, Y., Cherry, S., Häder, S., Gayko, U., and Perrimon, N. (2004) Temperature-sensitive control of protein activity by conditionally splicing inteins, *Nature biotechnology* 22, 871-876.

(31) Buskirk, A. R., Ong, Y.-C., Gartner, Z. J., and Liu, D. R. (2004) Directed evolution of ligand dependence: small-molecule-activated protein splicing, *Proceedings of the National Academy of Sciences of the United States of America* 101, 10505-10510.

(32) Shusta, E. V., Raines, R. T., Plückthun, A., and Wittrup, K. D. (1998) Increasing the secretory capacity of *Saccharomyces cerevisiae* for production of single-chain antibody fragments, *Nature biotechnology* 16, 773-777.

(33) Lorimer, I. A., Keppler-Hafkemeyer, A., Beers, R. A., Pegram, C. N., Bigner, D. D., and Pastan, I. (1996) Recombinant immunotoxins specific for a mutant epidermal growth factor receptor: targeting with a single chain antibody variable domain isolated by phage display, *Proceedings of the National Academy of Sciences* 93, 14815-14820.

(34) Zhou, Y., Drummond, D. C., Zou, H., Hayes, M. E., Adams, G. P., Kirpotin, D. B., and Marks, J. D. (2007) Impact of Single-chain Fv Antibody Fragment Affinity on Nanoparticle Targeting of Epidermal Growth Factor Receptor-expressing Tumor Cells, *Journal of Molecular Biology* 371, 934-947.

(35) Marks, J. D., and Zhou, Y. (2010) Mutant antibodies with high affinity for EGFR, US2010/0009390.

(36) Wang, X. X., Cho, Y. K., and Shusta, E. V. (2007) Mining a yeast library for brain endothelial cell-binding antibodies, *Nature methods* 4, 143-145.

(37) Hackel, B. J., Huang, D., Bubolz, J. C., Wang, X. X., and Shusta, E. V. (2006) Production of soluble and active transferrin receptor-targeting single-chain antibody using *Saccharomyces cerevisiae, Pharmaceutical research* 23, 790-797.

(38) Gietz, R. D., and Schiestl, R. H. (2007) High-efficiency yeast transformation using the LiAc/SS carrier DNA/PEG method, *Nature protocols* 2, 31-34.

(39) Zaccolo, M., Williams, D. M., Brown, D. M., and Gherardi, E. (1996) An approach to random mutagenesis of DNA using mixtures of triphosphate derivatives of nucleoside analogues, *Journal of molecular biology* 255, 589-603.

(40) Ness, J. E., Kim, S., Gottman, A., Pak, R., Krebber, A., Borchert, T. V., Govindarajan, S., Mundorff, E. C., and Minshull, J. (2002) Synthetic shuffling expands functional protein diversity by allowing amino acids to recombine independently, *Nature biotechnology* 20, 1251-1255.

(41) Stemmer, W. P., Crameri, A., Ha, K. D., Brennan, T. M., and Heyneker, H. L. (1995) Single-step assembly of a gene and entire plasmid from large numbers of oligodeoxyribonucleotides, *Gene* 164, 49-53.

(42) Wiepz, G., Guadaramma, A., Fulgham, D., and Bertics, P. (2006) Purification and assay of kinase-active EGF receptor from mammalian cells by immunoaffinity chromatography, *Methods in molecular biology* 327, 25.

(43) Cho, Y. K., Chen, I., Wei, X., Li, L., and Shusta, E. V. (2009) A yeast display immunoprecipitation method for efficient isolation and characterization of antigens, *Journal of immunological methods* 341, 117-126.

(44) Boder, E. T., Midelfort, K. S., and Wittrup, K. D. (2000) Directed evolution of antibody fragments with monovalent femtomolar antigen-binding affinity, *Proceedings of the National Academy of Sciences* 97, 10701-10705.

(45) Romanelli, A., Shekhtman, A., Cowburn, D., and Muir, T. W. (2004) Semisynthesis of a segmental isotopically labeled protein splicing precursor: NMR evidence for an unusual peptide bond at the N-extein-intein junction, *Proceedings of the National Academy of Sciences of the United States of America* 101, 6397-6402.

(46) Hyland, S., Beerli, R. R., Barbas, C. F., Hynes, N. E., and Wels, W. (2003) Generation and functional characterization of intracellular antibodies interacting with the kinase domain of human EGF receptor, *Oncogene* 22, 1557-1567.

(47) Wentz, A. E., and Shusta, E. V. (2007) A novel high-throughput screen reveals yeast genes that increase secretion of heterologous proteins, *Applied and environmental microbiology* 73, 1189-1198.

(48) Guo, J. Q., Li, Q. M., Zhou, J. Y., Zhang, G. P., Yang, Y. Y., Xing, G. X., Zhao, D., You, S. Y., and Zhang, C. Y. (2006) Efficient recovery of the functional IP10-scFv fusion protein from inclusion bodies with an on-column refolding system, *Protein Expression and Purification* 45, 168-174.

(49) Kipriyanov, S. M., Moldenhauer, G., and Little, M. (1997) High level production of soluble single chain antibodies in small-scale *Escherichia coli* cultures, *Journal of Immunological Methods* 200, 69-77.

(50) Verma, R., Boleti, E., and George, A. (1998) Antibody engineering: comparison of bacterial, yeast, insect and mammalian expression systems, *Journal of immunological methods* 216, 165-181.

(51) Tsumoto, K., Ogasahara, K., Ueda, Y., Watanabe, K., Yutani, K., and Kumagai, I. (1995) Role of Tyr residues in the contact region of anti-lysozyme monoclonal antibody HyHEL10 for antigen binding, *Journal of Biological Chemistry* 270, 18551-18557.

(52) Miller, K. D., Weaver-Feldhaus, J., Gray, S. A., Siegel, R. W., and Feldhaus, M. J. (2005) Production, purification, and characterization of human scFv antibodies expressed in *Saccharomyces cerevisiae, Pichia pastoris*, and *Escherichia coli, Protein expression and purification* 42, 255-267.

(53) Evans, T. C., Benner, J., and Xu, M. Q. (1998) Semisynthesis of cytotoxic proteins using a modified protein splicing element, *Protein Science* 7, 2256-2264.

(54) Southworth, M. W., Amaya, K., Evans, T. C., Xu, M.-Q., and Perler, F. B. (1999) Purification of proteins fused to either the amino or carboxy terminus of the *Mycobacterium xenopi* gyrase A intein, *Biotechniques* 27, 110-114, 116, 118-120.

(55) Rostovtsev, V. V., Green, L. G., Fokin, V. V., and Sharpless, K. B. (2002) A stepwise huisgen cycloaddition process: copper (I)-catalyzed regioselective "ligation" of azides and terminal alkynes, *Angewandte Chemie* 114, 2708-2711.

(56) Kalia, J., and Raines, R. T. (2010) Advances in bioconjugation, *Current organic chemistry* 14, 138.

(57) Speers, A. E., Adam, G. C., and Cravatt, B. F. (2003) Activity-based protein profiling in vivo using a copper (I)-catalyzed azide-alkyne[3+2] cycloaddition, *Journal of the American Chemical Society* 125, 4686-4687.

(58) Hong, V., Steinmetz, N. F., Manchester, M., and Finn, M. G. (2010) Labeling Live Cells by Copper-Catalyzed Alkyne-Azide Click Chemistry, *Bioconjugate Chemistry* 21, 1912-1916.

(59) Agard, N. J., Prescher, J. A., and Bertozzi, C. R. (2004) A Strain-Promoted [3+2] Azide-Alkyne Cycloaddition for Covalent Modification of Biomolecules in Living Systems, *Journal of the American Chemical Society* 126, 15046-15047.

(60) Dennler, P., Chiotellis, A., Fischer, E., Brégeon, D., Belmant, C., Gauthier, L., Lhospice, F., Romagne, F., and Schibli, R. (2014) Transglutaminase-Based Chemo-Enzymatic Conjugation Approach Yields Homogeneous Antibody-Drug Conjugates, *Bioconjugate Chemistry* 25, 569-578.

(61) Thomas, J. D., Cui, H., North, P., J, Hofer, T., Rader, C., and Burke Jr, T. R. (2012) Application of Strain-Promoted Azide-Alkyne Cycloaddition and Tetrazine Ligation to Targeted Fc-Drug Conjugates, *Bioconjugate chemistry* 23, 2007-2013.

(62) Colombo, M., Sommaruga, S., Mazzucchelli, S., Polito, L., Verderio, P., Galeffi, P., Corsi, F., Tortora, P., and Prosperi, D. (2012) Site-Specific Conjugation of ScFvs Antibodies to Nanoparticles by Bioorthogonal Strain-Promoted Alkyne-Nitrone Cycloaddition, *Angewandte Chemie* 124, 511-514.
(63) Kotagiri, N., Li, Z., Xu, X., Mondal, S., Nehorai, A., and Achilefu, S. (2014) Antibody Quantum Dot Conjugates Developed via Copper-Free Click Chemistry for Rapid Analysis of Biological Samples Using a Microflu-idic Microsphere Array System, *Bioconjugate Chemistry* 25, 1272-1281.
(64) Klabunde, T., Sharma, S., Telenti, A., Jacobs, W. R., and Sacchettini, J. C. (1998) Crystal structure of GyrA intein from *Mycobacterium xenopi* reveals structural basis of protein splicing, *Nature Structural & Molecular Biology* 5, 31-36.

We claim:

1. A non-self-cleaving Mxe GyrA intein having the amino acid sequence set forth in SEQ ID NO: 4 or having amino acid substitutions at amino acid positions Phe51, Ile105, Arg107, Phe110, Phe117, Phe124, Ser168 and Ile190 in the amino acid sequence set forth in SEQ ID NO: 2.

2. A nucleic acid molecule encoding a non-self-cleaving Mxe GyrA intein having the amino acid sequence set forth in SEQ ID NO: 4 or having amino acid substitutions at amino acid positions Phe51, Ile105, Arg107, Phe110, Phe117, Phe124, Ser168 and Ile190 in the amino acid sequence set forth in SEQ ID NO: 2.

3. The nucleic acid molecule of claim 2, wherein said nucleic acid molecule has the nucleotide, sequence set forth in SEQ ID NO: 3.

4. An expression vector comprising the nucleic acid molecule of claim 2.

5. The expression vector encoding a fusion protein, wherein said fusion protein comprises a non-self-cleaving Mxe GyrA intein having the amino acid sequence set forth in SEQ ID NO: 4 or having amino acid substitutions at amino acid positions Phe51, Ile105, Arg107, Phe110, Phe117, Phe124, Ser168 and Ile190 in the amino acid sequence set forth in SEQ ID NO: 2 and a protein of interest.

6. A host cell transformed with the expression vector of claim 4.

7. The host cell of claim 6, wherein said host cell is selected from the group consisting of a bacterial cell, a yeast cell, a mammalian cell, and a fungal cell.

8. The host cell of claim 7, wherein said host cell is a yeast cell.

9. A host cell transformed with the expression vector of claim 5.

10. The host cell of claim 9, wherein said host cell is selected from the group consisting of a bacterial cell, a yeast cell, a mammalian cell, and a fungal cell.

11. The host cell of claim 10, wherein said host cell is a yeast cell.

12. A method for chemically functionalizing a protein of interest in a host cell, the method comprising the steps of:
(a) culturing a host cell, said host cell being transformed with an expression vector encoding a fusion protein, wherein said fusion protein comprises a non-self-cleaving Mxe GyrA intein having the amino acid sequence set forth in SEQ ID NO: 4 or having amino acid substitutions at amino acid positions Phe51, Ile105, Arg107, Phe110, Phe117, Phe124, Ser168 and Ile190 in the amino acid sequence set forth in SEQ ID NO: 2 and a protein of interest;
(b) expressing the fusion protein in said host cell; and
(c) exposing said fusion protein to a compound having a nucleophile and a functional group, wherein the nucleophile of the compound reacts with the fusion protein to release the protein of interest from the fusion protein, wherein the protein of interest is chemically linked to the functional group.

13. The method of claim 12, wherein the host is selected from the group consisting of bacterial cells, yeast cells, mammalian cells, and fungal cells.

14. The method of claim 13, wherein said host cell is a yeast cell.

15. The method of claim 12, wherein the compound is 2-mercapthoethanesulfonic acid (MESNA).

16. The method of claim 12, wherein the protein is chemically functionalized via expressed protein ligation (EPL).

17. The method of claim 12, where the fusion protein expressed in step (b) is further purified.

18. A non-self-cleaving Mxe GyrA intein having the amino acid sequence set forth in SEQ ID NO: 6 or having amino acid substitutions at amino acid positions Val112, Cys114, Ala118, His144, Ser168, and Ile190 in the amino acid sequence set forth in SEQ ID NO: 2.

19. A nucleic acid molecule encoding a non-self-cleaving Mxe GyrA intein having the amino acid sequence set forth in SEQ ID NO: 6 or having amino acid substitutions at amino acid positions Val112, Cys114, Ala118, His144, Ser168 and Ile190 in the amino acid sequence set forth in SEQ ID NO: 2.

20. The nucleic acid molecule of claim 19, wherein said nucleic acid molecule has the nucleotide sequence set forth in SEQ ID NO: 5.

21. An expression vector comprising the nucleic acid molecule of claim 19.

22. The expression vector encoding a fusion protein, wherein said fusion protein comprises a non-self-cleaving Mxe GyrA intein having the amino acid sequence set forth in SEQ ID NO: 6 or having amino acid substitutions at amino acid positions Val112, Cys114, Ala118, His144, Ser168, and Ile190 in the amino acid sequence set forth in SEQ ID NO: 2 and a protein of interest.

23. A host cell transformed with the expression vector of claim 21.

24. The host cell of claim 23, wherein said host cell is selected from the group consisting of a bacterial cell, a yeast cell, a mammalian cell, and a fungal cell.

25. The host cell of claim 24, wherein said host cell is a yeast cell.

26. A host cell transformed with the expression vector of claim 22.

27. The host cell of claim 26, wherein said host cell is selected from the group consisting of a bacterial cell, a yeast cell, a mammalian cell, and a fungal cell.

28. The host cell of claim 27, wherein said host cell is a yeast cell.

29. A method for chemically functionalizing a protein of interest in a host cell, the method comprising the steps of:
(a) culturing a host cell, said host cell being transformed with an expression vector encoding a fusion protein, wherein said fusion protein comprises a non-self-cleaving Mxe GyrA intein having the amino acid sequence set forth in SEQ ID NO: 6 or having amino acid substitutions at amino acid positions Val112, Cys114, Ala118, His144, Ser168, and Ile190 in the amino acid sequence set forth in SEQ ID NO: 2 and a protein of interest;
(b) expressing the fusion protein in said host cell; and
(c) exposing said fusion protein to a compound having a nucleophile and a functional group, wherein the nucleophile of the compound reacts with the fusion protein to release the protein of interest from the fusion protein, wherein the protein of interest is chemically linked to the functional group.

30. The method of claim 29, wherein the host is selected from the group consisting of bacterial cells, yeast cells, mammalian cells, and fungal cells.

31. The method of claim 30, wherein said host cell is a yeast cell.

32. The method of claim 29, wherein the compound is 2-mercapthoethanesulfonic acid (MESNA).

33. The method of claim 29, wherein the protein is chemically functionalized via expressed protein ligation (EPL).

34. The method of claim 29, where the fusion protein expressed in step (b) is further purified.

35. A non-self-cleaving Mxe GyrA intein having the amino acid sequence set forth in SEQ ID NO: 8 or having amino acid substitutions at amino acid positions Arg107, Phe110, Cyst114, Ala118, Tyr129, His144, Asp158, and Arg160 in the amino acid sequence set forth in SEQ ID NO: 2.

36. A nucleic acid molecule encoding a non-self-cleaving Mxe GyrA intein having the amino acid sequence set forth in SEQ ID NO: 8 or having amino acid substitutions at amino acid positions Arg107, Phe110, Cys114, Ala118, Tyr129, His144, Asp158, and Arg160 in the amino add sequence set forth in SEQ ID NO: 2.

37. The nucleic acid molecule of claim 36, wherein said nucleic acid molecule has the nucleotide sequence set forth in SEQ ID NO: 7.

38. An expression vector comprising the nucleic acid molecule of claim 36.

39. An expression vector encoding a fusion protein, wherein said fusion protein comprises a non-self-cleaving Mxe GyrA intein having the amino acid sequence set forth in SEQ ID NO: 8 or having amino acid substitutions at amino acid positions Arg107, Phe110, Cys114, Ala118, Tyr129, His144, Asp158, and Arg160 in the amino acid sequence set forth in SEQ ID NO: 2 and a protein of interest.

40. A host cell transformed with the expression vector of claim 38.

41. The host cell of claim 40, wherein said host cell is selected from the group consisting of a bacterial cell, a yeast cell, a mammalian cell, and a fungal cell.

42. The host cell of claim 41, wherein said host cell is a yeast cell.

43. A host cell transformed with the expression vector of claim 39.

44. The host cell of claim 43, wherein said host cell is selected from the group consisting of a bacterial cell, a yeast cell, a mammalian cell, and a fungal cell.

45. The host cell of claim 44, wherein said host cell is a yeast cell.

46. A method for chemically functionalizing a protein of interest in a host cell, the method comprising the steps of:
  (a) culturing a host cell, said host cell being transformed with an expression vector encoding a fusion protein, wherein said fusion protein comprises a non-self-cleaving Mxe GyrA intein having the amino acid sequence set forth in SEQ ID NO: 8 or having amino acid substitutions at amino acid positions Arg107, Phe110, Cys114, Ala118, Tyr129, His144, Asp158, and Arg160 in the amino acid sequence set forth in SEQ ID NO: 2, in the amino acid sequence set forth in SEQ ID NO: 2 and a protein of interest;
  (b) expressing the fusion protein in said host cell; and
  (c) exposing said fusion protein to a compound having a nucleophile and a functional group, wherein the nucleophile of the compound reacts with the fusion protein to release the protein of interest from the fusion protein, wherein the protein of interest is chemically linked to the functional group.

47. The method of claim 46, wherein the host is selected from the group consisting of bacterial cells, yeast cells, mammalian cells, and fungal cells.

48. The method of claim 47, wherein said host cell is a yeast cell.

49. The method of claim 46, wherein the compound is 2-mercapthoethanesulfonic acid (MESNA).

50. The method of claim 46, wherein the protein is chemically functionalized via expressed protein ligation (EPL).

51. The method of claim 46. where the fusion protein expressed in step (b) is further purified.

* * * * *

UNITED STATES PATENT AND TRADEMARK OFFICE
CERTIFICATE OF CORRECTION

PATENT NO. : 9,771,412 B2
APPLICATION NO. : 14/926665
DATED : September 26, 2017
INVENTOR(S) : Eric V Shusta et al.

Page 1 of 1

It is certified that error appears in the above-identified patent and that said Letters Patent is hereby corrected as shown below:

In the Claims

Column 48, Claim 35, Line 40, "Cyst114" should be --Cys144--.

Column 48, Claim 36, Line 47, "add" should be --acid--.

Signed and Sealed this
Ninth Day of July, 2019

Andrei Iancu
*Director of the United States Patent and Trademark Office*

SEQUENCE LISTING

```
<160> NUMBER OF SEQ ID NOS: 12

<210> SEQ ID NO 1
<211> LENGTH: 594
<212> TYPE: DNA
<213> ORGANISM: Mycobacterium xenopi

<400> SEQUENCE: 1
tgcatcacgg gagatgcact agttgcccta cccgagggcg agtcggtacg catcgccgac     60
atcgtgccgg gtgcgcggcc caacagtgac aacgccatcg acctgaaagt ccttgaccgg    120
catggcaatc ccgtgctcgc cgaccggctg ttccactccg gcgagcatcc ggtgtacacg    180
gtgcgtacgg tcgaaggtct gcgtgtgacg ggcaccgcga accacccgtt gttgtgtttg    240
gtcgacgtcg ccggggtgcc gaccctgctg tggaagctga tcgacgaaat caagcccggc    300
gattacgcgg tgattcaacg cagcgcattc agcgtcgact gtgcaggttt tgcccgcggg    360
aaacccgaat ttgcgcccac aacctacaca gtcgccgtcc ctggactggt gcgtttcttg    420
gaagcacacc accgagaccc ggacgcccaa gctatcgccg acgagctgac cgacgggcgg    480
ttctactacg cgaaagtcgc cagtgtcacc gacgccggcg tgcagccggt gtatagcctt    540
cgtgtcgaca cggcagacca cgcgtttatc acgaacgggt tcgtcagcca cgct           594

<210> SEQ ID NO 2
<211> LENGTH: 198
<212> TYPE: PRT
<213> ORGANISM: Mycobacterium xenopi

<400> SEQUENCE: 2

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Ser Ala Phe Ser Val
            100                 105                 110

Asp Cys Ala Gly Phe Ala Arg Gly Lys Pro Glu Phe Ala Pro Thr Thr
        115                 120                 125

Tyr Thr Val Gly Val Pro Gly Leu Val Arg Phe Leu Glu Ala His His
    130                 135                 140

Arg Asp Pro Asp Ala Gln Ala Ile Ala Asp Glu Leu Thr Asp Gly Arg
145                 150                 155                 160
```

```
Phe Tyr Tyr Ala Lys Val Ala Ser Val Thr Asp Ala Gly Val Gln Pro
                165                 170                 175

Val Tyr Ser Leu Arg Val Asp Thr Ala Asp His Ala Phe Ile Thr Asn
            180                 185                 190

Gly Phe Val Ser His Ala
            195

<210> SEQ ID NO 3
<211> LENGTH: 594
<212> TYPE: DNA
<213> ORGANISM: Artificial Sequence
<220> FEATURE:
<223> OTHER INFORMATION: Clone 202-08

<400> SEQUENCE: 3
tgcatcacgg gagatgcact agttgcccta cccgagggcg agtcggtacg catcgccgac      60
atcgtgccgg gtgcgcggcc caacagtgac aacgccatcg acctgaaagt ccttgaccgg    120
catggcaatc ccgtgctcgc cgaccggctg ctccactccg gcgagcatcc ggtgtacacg    180
gtgcgtacgg tcgaaggtct gcgtgtgacg ggcaccgcga accaccgtt gttgtgtttg    240 gtcgacgtcg ccggggtgcc gaccctgctg tggaagctga tcgacgagat caagccgggc    300
gattacgcgg tggttcaatg cagcgcatcc agcgtcgact gtgcaggtct tgcccgcggg    360
aaacccgaac ttgcgcccac aacctacaca gtcggcgtcc ctggactggt gcgtttcttg    420
gaagcacacc accgagaccc ggacgcccaa gctatcgccg acgagctgac cgacgggcgg    480
ttctactacg cgaaagtcgc cggtgtcacc gacgccggcg tgcagccggt gtatagcctt    540
cgtgtcgaca cggcagacca cgcgtttacc acgaacgggt tcgtcagcca cgct          594

<210> SEQ ID NO 4
<211> LENGTH: 198
<212> TYPE: PRT
<213> ORGANISM: Artificial Sequence
<220> FEATURE:
<223> OTHER INFORMATION: Clone 202-08

<400> SEQUENCE: 4

Cys Ile Thr Gly Asp Ala Leu Val Ala Leu Pro Glu Gly Glu Ser Val
  1               5                  10                  15

Arg Ile Ala Asp Ile Val Pro Gly Ala Arg Pro Asn Ser Asp Asn Ala
                 20                  25                  30

Ile Asp Leu Lys Val Leu Asp Arg His Gly Asn Pro Val Leu Ala Asp
             35                  40                  45

Arg Leu Leu His Ser Gly Glu His Pro Val Tyr Thr Val Arg Thr Val
 50                  55                  60

Glu Gly Leu Arg Val Thr Gly Thr Ala Asn His Pro Leu Leu Cys Leu
 65                  70                  75                  80

Val Asp Val Ala Gly Val Pro Thr Leu Leu Trp Lys Leu Ile Asp Glu
                 85                  90                  95

Ile Lys Pro Gly Asp Tyr Ala Val Val Gln Cys Ser Ala Ser Ser Val
            100                 105                 110

Asp Cys Ala Gly Leu Ala Arg Gly Lys Pro Glu Leu Ala Pro Thr Thr
        115                 120                 125

Tyr Thr Val Gly Val Pro Gly Leu Val Arg Phe Leu Glu Ala His His
    130                 135                 140

Arg Asp Pro Asp Ala Gln Ala Ile Ala Asp Glu Leu Thr Asp Gly Arg
145                 150                 155                 160
```

Phe Tyr Tyr Ala Lys Val Ala Gly Val Thr Asp Ala Gly Val Gln Pro
                165                 170                 175

Val Tyr Ser Leu Arg Val Asp Thr Ala Asp His Ala Phe Thr Thr Asn
            180                 185                 190

Gly Phe Val Ser His Ala
        195

<210> SEQ ID NO 5
<211> LENGTH: 594
<212> TYPE: DNA
<213> ORGANISM: Artificial Sequence
<220> FEATURE:
<223> OTHER INFORMATION: Clone F2-02

<400> SEQUENCE: 5

```
tgcatcacgg gagatgcact agttgcccta cccgagggcg agtcggtacg catcgccgac    60
atcgtgccgg gtgcgcggcc caacagtgac aacgccatcg acctgaaagt ccttgatcgg   120
catggcaatc ccgtgctcgc cgaccggctg ttccactccg gcgagcatcc ggtgtacacg   180
gtgcgtacgg tcgaaggtct gcgtgtgacg ggcaccgcga accaccgtt gttgtgtttg    240 gtcgacgtcg ccggggtgcc gaccctgctg tggaagctga tcgacgaaat caagccgggc   300
gattacgcgg tgattcaacg cagcgcattc agcgccgacc gtgcaggttt tacccgcggg   360
aaacccgaat ttgcgcccac aacctacaca gtcggcgtcc ctggactggt gcgtttcttg   420
gaagcacacc gccgagaccc ggacgcccaa gctatcgccg acgagctgac cgacgggcgg   480
ttctactacg cgaaagtcgc cggtgtcacc gacgccggcg tgcagccggt gtatagcctt   540
cgtgtcgaca cggcagacca cgcgtttacc acgaacgggt tcgtcagcca cgct         594
```

<210> SEQ ID NO 6
<211> LENGTH: 198
<212> TYPE: PRT
<213> ORGANISM: Artificial Sequence
<220> FEATURE:
<223> OTHER INFORMATION: Clone F2-02

<400> SEQUENCE: 6

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Ser Ala Phe Ser Ala
            100                 105                 110

Asp Arg Ala Gly Phe Thr Arg Gly Lys Pro Glu Phe Ala Pro Thr Thr
        115                 120                 125

Tyr Thr Val Gly Val Pro Gly Leu Val Arg Phe Leu Glu Ala His Arg
    130                 135                 140

Arg Asp Pro Asp Ala Gln Ala Ile Ala Asp Glu Leu Thr Asp Gly Arg
145                 150                 155                 160

Phe Tyr Tyr Ala Lys Val Ala Gly Val Thr Asp Ala Gly Val Gln Pro
                165                 170                 175

Val Tyr Ser Leu Arg Val Asp Thr Ala Asp His Ala Phe Thr Thr Asn
            180                 185                 190

Gly Phe Val Ser His Ala
            195

<210> SEQ ID NO 7
<211> LENGTH: 594
<212> TYPE: DNA
<213> ORGANISM: Artificial Sequence
<220> FEATURE:
<223> OTHER INFORMATION: Clone F5-06

<400> SEQUENCE: 7
tgcatcacgg gagatgcact agttgcccta cccgagggcg agtcggtacg catcgccggc        60
atcgtgccgg gtgcgcggcc aacagtgac aacgccatcg acctgaaagt ccttgaccgg       120
catggcaatc ccgtgctcgc cgaccggctg ttccactccg gcgagcatcc ggtgtacacg       180
gtgcgtacgg tcgaaggtct gcgtgtgacg ggcaccgcga accaccgtt gttgtgtttg       240 gtcgacgtcg ccggggtgcc gaccctgctg tggaagctga tcgacgaaat caagccgggc       300
gattacgcgg tgattcaatg cagcgcatcc agcgtcgacg gtgcaggttt tacccgcggg       360
aaacccgaat ttgcgcccac aacctgcaca gtcggcgtcc ctggactggt gcgtttcttg       420
gaagcacacc gccgagaccc ggacgcccaa gctatcgccg acgagctgac cggcgggcag       480
ttctactacg cgaaggtcgc cagtgtcacc gacgccggcg tgcagccggt gtatagcctt       540
cgtgtcgaca cggcagacca cgcgtttatc acgaacgggt tcgtcagcca cgct             594

<210> SEQ ID NO 8
<211> LENGTH: 198
<212> TYPE: PRT
<213> ORGANISM: Artificial Sequence
<220> FEATURE:
<223> OTHER INFORMATION: Clone F5-06

<400> SEQUENCE: 8

Cys Ile Thr Gly Asp Ala Leu Val Ala Leu Pro Glu Gly Glu Ser Val
  1                 5                  10                 15

Arg Ile Ala Gly Ile Val Pro Gly Ala Arg Pro Asn Ser Asp Asn Ala
             20                 25                 30

Ile Asp Leu Lys Val Leu Asp Arg His Gly Asn Pro Val Leu Ala Asp
             35                 40                 45

Arg Leu Phe His Ser Gly Glu His Pro Val Tyr Thr Val Arg Thr Val
 50                 55                 60

Glu Gly Leu Arg Val Thr Gly Thr Ala Asn His Pro Leu Leu Cys Leu
 65                 70                 75                 80

Val Asp Val Ala Gly Val Pro Thr Leu Leu Trp Lys Leu Ile Asp Glu
             85                 90                 95

Ile Lys Pro Gly Asp Tyr Ala Val Ile Gln Cys Ser Ala Ser Ser Val
            100                105                110

Asp Gly Ala Gly Phe Thr Arg Gly Lys Pro Glu Phe Ala Pro Thr Thr
            115                120                125

Cys Thr Val Gly Val Pro Gly Leu Val Arg Phe Leu Glu Ala His Arg
            130                135                140

Arg Asp Pro Asp Ala Gln Ala Ile Ala Asp Glu Leu Thr Gly Gly Gln
145                 150                155                160

```
Phe Tyr Tyr Ala Lys Val Ala Ser Val Thr Asp Ala Gly Val Gln Pro
                165                 170                 175

Val Tyr Ser Leu Arg Val Asp Thr Ala Asp His Ala Phe Ile Thr Asn
        180                 185                 190

Gly Phe Val Ser His Ala
        195

<210> SEQ ID NO 9
<211> LENGTH: 50
<212> TYPE: DNA
<213> ORGANISM: Artificial Sequence
<220> FEATURE:
<223> OTHER INFORMATION: synthetic

<400> SEQUENCE: 9
cagaacaaaa gcttatttct gaagaagact tggcggccgc cggctgcatc            50

<210> SEQ ID NO 10
<211> LENGTH: 50
<212> TYPE: DNA
<213> ORGANISM: Artificial Sequence
<220> FEATURE:
<223> OTHER INFORMATION: synthetic

<400> SEQUENCE: 10
ggtggtggtg gttctggtgg tggtggttct ggtggtggtg gttctggatc            50

<210> SEQ ID NO 11
<211> LENGTH: 22
<212> TYPE: DNA
<213> ORGANISM: Artificial Sequence
<220> FEATURE:
<223> OTHER INFORMATION: synthetic

<400> SEQUENCE: 11
tctgtgaaag gcagattcac ca                                          22

<210> SEQ ID NO 12
<211> LENGTH: 21
<212> TYPE: DNA
<213> ORGANISM: Artificial Sequence
<220> FEATURE:
<223> OTHER INFORMATION: synthetic

<400> SEQUENCE: 12
acaaagagta cggcgtcgat t                                           21
```